(12) United States Patent
Keating et al.

(10) Patent No.: US 11,198,715 B2
(45) Date of Patent: Dec. 14, 2021

(54) SELECTIVE BFL-1 PEPTIDES

(71) Applicant: MASSACHUSETTS INSTITUTE OF TECHNOLOGY, Cambridge, MA (US)

(72) Inventors: Amy Keating, Arlington, MA (US); Justin Michael Jenson, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 16/319,199

(22) PCT Filed: Jul. 21, 2017

(86) PCT No.: PCT/US2017/043219
§ 371 (c)(1),
(2) Date: Jan. 18, 2019

(87) PCT Pub. No.: WO2018/017922
PCT Pub. Date: Jan. 25, 2018

(65) Prior Publication Data
US 2019/0185531 A1    Jun. 20, 2019

Related U.S. Application Data

(60) Provisional application No. 62/365,484, filed on Jul. 22, 2016, provisional application No. 62/517,146, filed on Jun. 8, 2017.

(51) Int. Cl.
| | | |
|---|---|---|
| *C07K 14/00* | (2006.01) | |
| *C07K 14/47* | (2006.01) | |
| *A61P 35/00* | (2006.01) | |
| *G01N 33/574* | (2006.01) | |
| *C07K 14/395* | (2006.01) | |
| *G01N 33/50* | (2006.01) | |
| *C07K 1/113* | (2006.01) | |
| *A61K 38/00* | (2006.01) | |

(52) U.S. Cl.
CPC .......... *C07K 14/4747* (2013.01); *A61P 35/00* (2018.01); *C07K 1/113* (2013.01); *C07K 14/00* (2013.01); *C07K 14/395* (2013.01); *G01N 33/50* (2013.01); *G01N 33/574* (2013.01); *A61K 38/00* (2013.01); *C07K 2319/00* (2013.01); *C07K 2319/10* (2013.01); *C07K 2319/42* (2013.01); *C07K 2319/43* (2013.01); *G01N 2333/4703* (2013.01)

(58) Field of Classification Search
None
See application file for complete search history.

(56) References Cited

U.S. PATENT DOCUMENTS

| | | |
|---|---|---|
| 5,446,090 A | 8/1995 | Harris |
| 6,348,558 B1 | 2/2002 | Harris et al. |
| 7,723,468 B2 | 5/2010 | Daffre et al. |
| 2004/0067503 A1 | 4/2004 | Tan et al. |
| 2005/0250680 A1 | 11/2005 | Walensky et al. |
| 2006/0073161 A1 | 4/2006 | Breton |
| 2008/0027145 A1* | 1/2008 | Huang ............... C07K 14/4747 514/789 |
| 2008/0199890 A1 | 8/2008 | Letai |
| 2009/0092582 A1 | 4/2009 | Bogin et al. |
| 2009/0275519 A1 | 11/2009 | Nash et al. |
| 2010/0273704 A1 | 10/2010 | Korsmeyer et al. |
| 2010/0286057 A1 | 11/2010 | Walensky et al. |
| 2012/0172285 A1 | 7/2012 | Walensky et al. |
| 2014/0363434 A1 | 12/2014 | Lasters et al. |
| 2015/0045310 A1 | 2/2015 | Link et al. |
| 2016/0095315 A1 | 4/2016 | Wei et al. |
| 2018/0128813 A1 | 5/2018 | Letai et al. |
| 2018/0201658 A1 | 7/2018 | Rezaci-Araghi et al. |
| 2019/0077840 A1 | 3/2019 | Rezaei-Araghi et al. |
| 2020/0262914 A1 | 8/2020 | Xue et al. |

FOREIGN PATENT DOCUMENTS

| | | |
|---|---|---|
| WO | WO 1997/028819 | 8/1997 |
| WO | WO 1999/014259 | 3/1999 |
| WO | WO 1999/034833 | 7/1999 |
| WO | WO 2006/000034 | 1/2006 |
| WO | WO2006/135985 | 12/2006 |
| WO | WO 2008/121767 | 10/2008 |
| WO | WO 2008/104000 | 11/2008 |
| WO | WO2010/060112 | 5/2010 |
| WO | WO 2010/068684 | 6/2010 |
| WO | WO2010/148335 | 12/2010 |
| WO | WO2013/116829 | 8/2013 |
| WO | WO 2016/149613 | 9/2016 |

OTHER PUBLICATIONS

Stebbins JL, Structure-based design of covalent Siah inhibitors, Chem Biol. Aug. 22, 2013;20(8):973-82 (Year: 2013).*

Adams et al., "Measuring the sequence-affinity landscape of antibodies with massively parallel titration curves," eLife, Dec. 30, 2016, 5, e23156.

Alford et al., "The Rosetta All-Atom Energy Function for Macromolecular Modeling and Design," Journal of Chemical Theory and Computation, Jun. 13, 2017, 13(6), 3031-3048.

Altschul et al., "Gapped BLAST and PSI-BLAST: a new generation of protein database search programs," Nucleic Acids Res., Sep. 1, 1997, 25: 3389-3402.

Araghi et al., "Rapid Optimization of Mcl-1 Inhibitors using Stapled Peptide Libraries Including Non-Natural Side Chains," ACS Chem. Biol., Epub. May 20, 2016 19, 11(5):1238-44; p. 1239, Table 1.

(Continued)

*Primary Examiner* — Thomas S Heard
(74) *Attorney, Agent, or Firm* — Fish & Richardson P.C.

(57) ABSTRACT

Provided herein are compounds comprising peptides that bind Bfl-1. Also provided are compositions containing these peptides and methods of using such peptides in the treatment of cancer that include administering to a subject one of the peptides.

16 Claims, 19 Drawing Sheets
Specification includes a Sequence Listing.

(56) References Cited

OTHER PUBLICATIONS

Arkadash et al., "Development of High Affinity and High Specificity Inhibitors of Matrix Metalloproteinase 14 through Computational Design and Directed Evolution," Journal of Biological Chemistry, Jan. 13, 2017, 292(8), 3481-3495.
Arkin et al., (2014). "Small-Molecule Inhibitors of Protein-Protein Interactions: Progressing toward the Reality," Chemistry & Biology, Sep. 18, 2014, 21(9), 1102-1114.
Armstrong et al., "The (i,i+4) Phe-His Interaction Studied in an Alanine-based α-Helix," Journal of Molecular Biology', Mar. 5, 1993, 230(1), 284, 1993.
Bedbrook et al., "Machine learning to design integral membrane channelrhodopsins for efficient eukaryotic expression and plasma membrane localization," PLOS Computational Biology, Oct. 23, 2017, 13(10), e1005786.
Berger et al., "Computationally designed high specificity inhibitors delineate the roles of BCL2 family proteins in cancer," eLife, Nov. 2, 2016, 5, 1422-1432.
Berman et al., "The Protein Data Bank," Nucleic Acids Research, Jan. 1, 2000, 28(1), 235-242.
biorxiv.org [online] Zhou et al., "A general-purpose protein design framework based on mining sequence-structure relationships in experimentally-derived protein structures," available Oct. 1, 2018, retrieved Oct. 2, 2019, retrieved from URL <https://www.biorxiv.org/content/10.1101/431635v1>, 15 pages.
Bird et al., "Biophysical determinants for cellular uptake of hydrocarbon-stapled peptide helices," Nature Chemical Biology, Aug. 22, 2016, 12(10), 845-852.
Bird et al., "Chemical Synthesis of Hydrocarbon-Stapled Peptides for Protein Interaction Research and Therapeutic Targeting," Current Protocols in Chemical Biology, Sep. 1, 2011, 99-117.
Blackwell et al., "Highly Efficient Synthesis of Covalently Cross-Linked Peptide Helices by Ring-Closing Metathesis," Angew Chem. Int. Ed. Dec. 1998, 37: 3281.
Blackwell et al., "Ring-Closing Metathesis of Olefinic Peptides: Design, Synthesis, and Structural Characterization of Macrocyclic Helical Peptides," J. Org. Chem., Aug. 10, 2001, 66: 5291-5302.
Boersma et al., "Hydrophile scanning as a complement to alanine scanning for exploring and manipulating protein-protein recognition: Application to the Bim BH3 domain," Protein Sci., Jul. 17, 2008, 17(7), 1232.
Bose et al., "Mcl-1 as a therapeutic target in acute myelogenous leukemia (AML)," Leukemia Research Reports, Jan. 1, 2013, 2(1), 12-14.
Burke et al., "Discovery of Trycyclic Indoles that Potently Inhibit Mcl-1 using Fragment-Based Methods and Structure-Based Design," J. Med. Chem., Apr. 17, 2015, 58(9), 3794.
Burnelle et al., "MCL-1-dependent leukemia cells are more sensitive to chemotherapy than BCL-2-dependent counterparts," J. Cell. Biol., Nov. 2, 2009, 187(3),429.
Cang et al., "ABT-199 (venetoclax) and BCL-2 inhibitors in clinical development," Journal of Hematology & Oncology, Dec. 2015, 8(1).
Chames et al., "Therapeutic antibodies: successes, limitations and hopes for the future," British Journal of Pharmacology. May 2009, 157: 220-33.
Chao et al., "Isolating and engineering human antibodies using yeast surface display," Nature Protocols, Aug. 2006, 1(2), 755-768.
Chatr-Aryamontri et al., "The BioGRID interaction database: 2017 update," Nucleic Acids Research, Jan. 4, 2017, 45(D1), D369-D379.
Chaudhury et al., "PyRosetta: a script-based interface for implementing molecular modeling algorithms using Rosetta," Bioinformatics, Jan. 7, 2010, 26(5), 689-691.
Chen et al., "Designing specific protein-protein interactions using computation, experimental library screening, or integrated methods," Protein Science, Jul. 2012, 21(7), 949-963.

Chen el al., "Structure-Based Redesign of the Binding Specificity of Anti-Apoptotic Bcl-xL," Journal of Molecular Biology, Jan. 9, 2013, 425(1), 171-185.
Chevalier et al., "Massively parallel de novo protein design for targeted therapeutics," Nature Publishing Group; Oct. 2017, 550: 74-79.
Chica et al., "Generation of longer emission wavelength red fluorescent proteins using computationally designed libraries," Proceedings of the National Academy of Sciences, Nov. 23, 2010, 107(47), 20257-20262.
Choi et al., "Bcl-xL promotes metastasis independent of its anti-apoptotic activity," Nature Communications, Jan. 20, 2016, 7, 10384.
Crooks et al., "WebLogo: A Sequence Logo Generator," Genome Research, 2004, 14(6), 1188-1190.
Davey et al., "Improving the accuracy of protein stability predictions with multistate design using a variety of backbone ensembles." Proteins: Structure, Function, and Bioinformatics. 2013. [82(5), 771-784.].
DeBartolo et al., "Predictive Bcl-2 Family Binding Models Rooted in Experiment or Structure," Journal of Molecular Biology, Sep. 7, 2012, 422(1), 124-144.
Deng et al., "BH3 Profiling Identifies Three Distinct Classes of Apoptotic Blocks to Predict Response to ABT-737 and Conventional Chemotherapeutic Agents," Cancer Cell, Aug. 14, 2007, 12(2), 171.
Dutta et al., "Determinants of BH3 Binding Specificity for Mcl-1 versus Bcl-xL," Journal of Molecular Biology, May 21, 2010, 398(5), 747-762.
Dutta et al., "Peptide Ligands for Pro-survival Protein Bfl-1 from Computationally Guided Library Screening," ACS Chemical Biology, Feb. 21, 2013, 8(4), 778-788.
Dutta et al., "Potent and Specific Peptide Inhibitors of Human Pro-Survival Protein Bcl-xL," Journal of Molecular Biology, Mar. 27, 2015, 427(6), 1241-1253.
Eckert et al., "Characterization of the steric defense of the HIV-1 gp41 N-trimer region," Protein Science, Dec. 2008, 17(12), 2091-2100.
Edgar"Search and clustering orders of magnitude faster than BLAST," Bioinformatics, Aug. 12, 2010, 26(19), 2460-2461.
Emsley et al., "Features and development of Coot," Acta Crystailographica Section D Biological Crystallography, Apr. 1, 2010, 66(4), 486-501.
European Supplementary Search Report, in Appln. No. EP16765822, dated Jul. 24, 2018, 22 pages.
Feng el al., "A topological and conformational stability alphabet for multipass membrane proteins," Nature Chemical Biology, Mar. 2016, 12(3), 167-173.
Fernandez-Fuentes et al., "A supersecondary structure library and search algorithm for modeling loops in protein structures," Nucleic Acids Research, Jan. 1, 2006, 34(7), 2085-2097.
Fire et al., "Mcl-1-Bim complexes accommodate surprising point mutations via minor structural changes," Protein Science, Mar. 2010, 19: 507-19.
Fleishman et al., "Computational Design of Proteins Targeting the Conserved Stem Region of Influenza Hemagglutinin," Science, May 13, 2011, 332(6031), 816-821.
Foight et al., "Locating Herpesvirus Bcl-2 Homologs in the Specificity Landscape of Anti-Apoptotic Bcl-2 Proteins," Journal of Molecular Biology, Jul. 31, 2015, 427(15), 2468-2490.
Fowler et al., "High-resolution mapping of protein sequence-function relationships," Nature Methods, Sep. 2010, 7(9), 741-746.
Frappier et al., "PixelDB: Protein-peptide complexes annotated with structural conservation of the peptide binding mode," Protein Science, Jan. 2018, 27(1), 276-285.
Gai et al., "Yeast surface display for protein engineering and characterization," Current Opinion in Structural Biology, Aug. 1, 2007 17(4), 467-473.
Gautier et al., "HELIQUEST: a web server to screen sequences with specific-helical properties," Bioinformatics, Jul. 28, 2008, 24(18), 2101-2102.

(56) References Cited

OTHER PUBLICATIONS

Gorelik et al., "Inhibition of SCF ubiquitin ligases by engineered ubiquitin variants that target the Cul1 binding site on the Skp1-F-box interface," Proceedings of the National Academy of Sciences, Mar. 29, 2016, 113(13), 3527-3532.

Grigoryan et al., "Design of protein-interaction specificity gives selective bZIP-binding peptides," Nature, Apr. 2009, 458(7240), 859-864.

He et al., "Compositional Bias in Naïve and Chemically-modified Phage-Displayed Libraries uncovered by Paired-end Deep Sequencing," Scientific Reports, Jan. 19, 2018, 8(1), 1214.

Henikoff et al., "Amino acid substitution matrices from protein blocks," Proceedings of the National Academy of Sciences, Nov. 15, 1992, 89(22), 10915-10919.

Hiraki et al., "Targeting MUC1-C suppresses BCL2A1 in triple-negative breast cancer," Signal Transduction and Targeted Therapy, May 12, 2018, 3(1).

Jacobs et al., "Design of structurally distinct proteins using strategies inspired by evolution," Science, May 6, 2016, 352(6286), 687-690.

Jacobs el al., "SwiftLib: rapid degenerate-codon-library optimization through dynamio programming," Nucleic Acids Research, Dec. 24, 2015, 43(5), e34-e34.

Jenson et al "Peptide design by optimization on a data-parameterized protein interaction landscape," Proceedings of the National Academy of Sciences, Oct. 30, 2018, 115(44):E10342-E10351.

Jenson et al., "Epistatic mutations in PUMA BH3 drive an alternate binding mode to potently and selectively inhibit anti-apoptotic Bfl-1," Elife, June 8, 2017, 6, e255741.

Karanicolas et al., "Computational design of affinity and specificity at protein-protein interfaces," Current Opinion in Structural Biology, Aug. 1, 2009, 19(4), 458-463.

Kawamoto et al., "Design of Triazole-stapled BCL9 a-Helical Peptides to Target the B-Catenin/B-cell CLL/lymphoma 9 (BCL9) Protein-Protein Interaction," Journal of Medicinal Chemistry Jan. 24, 2012, 55:1137-1146.

Kim et al., "Synthesis of all-hydrocarbon stapled a-helical peptides by ring-closing olefin metathesis," Nat. Protoc., Jun. 2011, 6(6), 761.

Kingsford et al., "Solving and analyzing side-chain positioning problems using linear and integer programming," Bioinformatics, Nov. 16, 2004, 21(7), 1028-1039.

Kotschy et al., "The MCL1 inhibitor S63845 is tolerable and effective in diverse cancer models." Nature, Oct. 2016, 538(7626), 477-482.

Kritzer, "Stapled Peptides: Magic bullets in nature's arsenal," Nature Chemical Biology, Aug. 2010, vol. 6, No. 8, 566-567.

Kuang et al., "DOMMINO 2.0: integrating structurally resolved protein-, RNA-, and DNA-mediated macromolecular interactions," Database, Jan. 1, 2016, 2016: 1-2.

Kumar et al., "Novel Polymeric Nanoparticles for Intracellular Delivery of Peptide Cargos: Antitumor Efficacy of the BCL-2 Conversion Peptide NuBCP-9," Cancer Research, Jun. 15, 2014, 74(12), 3271-3281.

Larkin et al., "Clustal W and Clustal X version 2.0," Bioinformatics, Nov. 1, 2007, 23(21), 2947-2948.

Lee et al., "Novel Bcl-2 Homology-3 Domain-like Sequences Identified from Screening Randomized Peptide Libraries for Inhibitors of the Pro-survival Bcl-2 Proteins," Journal of Biological Chemistry, Nov. 6, 2009, 284(45), 31315-31326.

Lessene et al., "Structure-guided design of a selective BCL-XL inhibitor," Nature Chemical Biology, Jun. 2013, 9(6), 390-397.

Lewis et al., "Anchored Design of Protein-Protein Interfaces," PLoS ONE, Jun. 17, 2011, 6(6), e20872.

Mackenzie et al., "Protein structural motifs in prediction and design," Current Opinion in Structural Biology, Jun. 1, 2017, 44, 161-167.

Mackenzie et al., "Tertiary alphabet for the observable protein structural universe." Proceedings of the National Academy of Sciences, Nov. 22, 2016, 113(47), E7438-E7447.

Malik et al., "Role of Capsid Structure and Membrane Protein Processing in Determining the Size and Copy Number of Peptides Displayed on the Major Coat Protein of Filamentous Bacteriophage," Journal of Molecular Biology, Jul. 5, 1996, 260(1), 9-21.

Matochko et al., "Prospective identification of parasitic sequences in phage display screens," Nucleic Acids Research, Nov. 9, 2013, 42(3), 1784-1798.

McConkey et al., "Discrimination of native protein structures using atom-atom contact scoring," Proceedings of the National Academy of Sciences, Mar. 18, 2003, 100(6), 3215-3220.

McCoy et al., "Phaser crystallographic software," Journal of Applied Crystallography, Aug. 1, 2007, 40(4):658-674.

Miles et al., "Hydrocarbon constrained peptides—understanding preorganisation and binding affinity," Chemical Science, 2016, 7(6), 3694-3702.

Moldoveanu et al., "Many players in BCL-2 family affairs," Trends in Biochemical Sciences, Mar. 1, 2014, 39(3), 101-111.

Montero et al., "Why do BCL-2 inhibitors work and where should we use them in the clinic?" Cell Death & Differentiation, Jan. 2018, 25(1), 56-64.

Muñoz et al., "Development of the multiple sequence approximation within the AGADIR model of α-helix formation: Comparison with Zimm-Bragg and Lifson-Roig formalisms," Biopolymers, Apr. 15, 1997, 41(5), 495-509.

Needleman et al., "A general method applicable to the search for similarities in the amino acid sequence of two proteins," Journal of Molecular Biology, Mar. 28, 1970 48(3), 443-453.

Negron et al., "A Set of Computationally Designed Orthogonal Antiparallel Homodimers that Expands the Synthetic Coiled-Coil Toolkit," Journal of the American Chemical Society, Nov. 13, 2014, 136(47), 16544-16556.

Nischan et al., "Covalent Attachment of Cyclic TAT Peptides to GFP Results in Protein Delivery into Live Cells with Immediate Bioavailability." Angewandte Chemie International Edition, Feb. 2, 2014, 54(6), 1950-1953.

Okamoto et al., "Stabilizing the pro-apoptotic BimBH3 helix (BimSAHB) does not necessarily enhance affinity or biological activity," ACS Chemical Biology, Feb. 15, 2013, 8(2):297-302.

Olsson et al., "Upregulation of bfl-1 is a potential mechanism of chemoresistance in B-cell chronic lymphocytic leukaemia," British Journal of Cancer, Sep. 2007, 97(6), 769-777.

Oltersdorf et al., "An inhibitor of Bcl-2 family proteins induces regression of solid tumours," Nature, Jun. 2005, 435(7042), 677-681.

Opferman, "Attacking cancer's Achilles heel: antagonism of anti-apoptotic BCL-2 family members," The FEES Journal, Jul. 1, 2015, 283(14), 2661-2675.

Otwinowski et al., "[20] Processing of X-ray diffraction data collected in oscillation mode," Methods Enzymol, Jan. 1, 1997, 276:307-326.

PCT International Search Report and Written Opinion in International Appln. No. PCT/US2019/51410, dated Feb. 18, 2020, 11 pages.

PCT International Search Report and Written Opinion in International Application No. PCT/US2016/059320, dated May 22, 2017, 10 pages.

PCT International Search Report and Written Opinion dated Sep. 23, 2016 in International Application No. PCT/US2016/023118, 17 pages.

PCT International Search Report, in International Application No. PCT/US2013/024617, dated Jun. 20, 2013, 3 pages.

Potapov et al., "Data-Driven Prediction and Design of bZIP Coiled-Coil Interactions," PLOS Computational Biology, Feb. 19, 2015, 11(2), e1004046.

Procko et al., "A Computationally Designed Inhibitor of an Epstein-Barr Viral Bcl-2 Protein Induces Apoptosis in Infected Cells," Cell, Jun. 19, 2014, 157(7), 1644-1656.

Reich et al "Generating High-Accuracy Peptide-Binding Data in High Throughput with Yeast Surface Display and SORTCERY," Computational Design of Ligand Binding Proteins, 2016, 233-247.

(56) References Cited

OTHER PUBLICATIONS

Reich et al., "SORTCERY—A High-Throughput Method to Affinity Rank Peptide Ligands." Journal of Molecular Biology, Jun. 5, 2015, 427(11), 2135-2150.
Rezaei et al., "Iterative optimization yields Mcl-1-targeting stapled peptides with selective cytotoxicity to Mcl-1-dependent cancer cells," Proceedings of the National Academy of Sciences, Jan. 30, 2018, 115(5), E886-E895.
Roberts et al., "Computational Design of a PDZ Domain Peptide Inhibitor that Rescues CFTR Activity," PLoS Computational Biology, Apr. 19, 2012, 8(4), e1002477.
Romero et al., "Navigating the protein fitness landscape with Gaussian processes," Proceedings of the National Academy of Sciences, Jan. 15, 2013, 110(3), E193-E201.
Roosenburg et al. "Stabilized 111 In-labeled sCCK8 analogues for targeting CCK2-receptor positive tumors: synthesis and evaluation," Bioconjugate Chem., Mar. 19, 2010, 21(4), 663-670.
Ryan et al., "BH3 profiling in whole cells by fluorimeter or FACS," Methods, Jun. 1, 2013, 61(2), 156-164.
Ryan el al., "Heightened mitochondrial priming is the basis for apopiotic hypersensitivity of CD4+ CD8+ thymocytes," Proc. Natl. Acad. Sci., Jun. 20, 2010, 107(29), 12895-900.
Ryvkin et al., "Phage display peptide libraries: deviations from randomness and correctives," Nucleic Acids Research, Feb. 6, 2018, 46(9), e52-e52.
Salvat et al., "Computationally optimized deimmunization libraries yield highly mutated enzymes with low immunogenicity and enhanced activity," Proceedings of the National Academy of Sciences, Jun. 27, 2017, 201621233.
Scherr et al., "Bcl-xL is an oncogenic driver in colorectal cancer," Cell Death & Disease, Aug. 2016, 7(8), e2342-e2342.
Schoenwaelder et al., "Bcl-xL-inhibitory BH3 mimetics can induce a transient thrombocytopathy that undermines die hemostatic function of platelets," Blood, Aug. 11, 2011, 118(6), 1663-1674.
Schwarze et al., "In Vivo Protein Transduction: Delivery of a Biologically Active Protein into the Mouse," Science, Sep. 3, 1999, 285(5433), 1569-1572.
Schymkowitz et al., "The FoldX web server: an online force field," Nucleic Acids Research, Jul. 1, 2005, 33 (Web Server), W382-W388.
Senft et al., "Selective Induction of Cell Death in Melanoma Cell Lines through Targeting of Mcl-1 and A1," PLoS ONE, Jan. 24, 2012, 7(1), e30821.
Shirian et al., "Converting a broad matrix metalloproteinase family inhibitor into a specific inhibitor of MMP-9 and MMP-14," FEBS Letters, Apr. 1, 2018 592(7), 1122-1134.
Smola et al., "A tutorial on support vector regression," Statistics and computing, Aug. 1, 2004, 14(3):199-222.
Souers et al., "ABT-199, a potent and selective BCL-2 inhibitor, achieves antitumor activity while sparing platelets," Nature Medicine, Feb. 2013, 19(2), 202-208.
Stewart et al., "The MCL-1 BH3 Helix is an Exclusive MCL-1 inhibitor and Apoptosis Sensitizer," Nat. Chem. Biol., Aug. 2010, 6(8),595.
Tompa et al., "A Million Peptide Motifs for the Molecular Biologist," Molecular Cell, Jul. 17, 2014, 55(2), 161-169.
UniProt Consortium, "UniProt: the universal protein knowledgebase," Nucleic Acids Research, Nov. 28, 2016, 45(D1), D158-D169.
Vanhee et al., "BrX: a database of protein building blocks for structural analysis, modeling and design," Nucleic Acids Research, Oct. 22, 2010, 39(suppl_1), D435-D442.
Verma et al., "Pareto optimization of combinatorial mutagenesis libraries," IEEE/ACM Transactions on Computational Biology and Bioinformatics, Jul. 23, 2018, 1-1.
Walensky et al., "Hydrocarbon-Stapled Peptides: Principles, Practice, and Progress," Journal of Medicinal Chemistry, Mar. 6, 2014, 57(15), 6275-6288.
Wang el al., "Alignment of distantly related protein structures: algorithm, bound and implications to homology modeling," Biomformatics, Jul. 26, 2011, 27(18), 2537-2545.

Wenzel et al., "MCL1 is deregulated in subgroups of diffuse large B-cell lymphoma," Leukemia, Jun. 2012, 27(6), 1381-1390.
Whitehead et al., "Optimization of affinity, specificity and function of designed influenza inhibitors using deep sequencing," Nature Biotechnology, Jun. 2012, 30(6), 543-548.
Wilen et al., "Tales of Resolving Agents and Optical Resolutions", p. 268, University of Notre Dame Press, 1972.
Williams et al., "Asymmetric Synthesis of Monosubstituted and a, a -Disubstituted—Amino Acids via Diastereoselective Glycine Enolate Alkylations," J. Am. Chem. Soc., Nov. 1991, 113: 9276.
Williams et al., "Efficient Asymmetric Synthesis of N-tert-Butoxycarbonyl □-Aminoacids Using 4-tert-Butoxycarbonyl-5,6-Diphenylmorpholin-2-One: (R)-(Ntert-Butoxycarbonyl)Allylglycine [(4-Pentenoic acid, 2-[[(1,1-dimethylethoxy)carbonyl]amino]-, (2R)-)]," Org. Synth., Apr. 28, 2003, 80:31.
Wong et al., "Direct visualization of Bcl-2 family protein interactions using live cell fluorescent protein redistribution assays," Cell death & disease, Mar. 3, 2012; 3(3):e288.
Xiao et al., "Immobilized OBOC combinatorial bead array to facilitate multiplicative screening," Comb. Chem. High Throughput Screen, Jul. 1, 2013, 16(6), 441.
Yecies et al., "Acquired resistance to ABT-737 in lymphoma cells that up-resulate MCL-1 and BFL-1," Blood, Apr. 22, 2010, 115(16), 3304-3313.
Zheng et al., "Computational Design of Selective Peptides to Discriminate between Similar PDZ Domains in an Oncogenic Pathway," Journal of Molecular Biology, Jan. 30, 2015, 427(2), 491-510.
Zheng et al., "Sequence statistics of tertiary structural motifs reflect protein stability," PLOS ONE, May 26, 2017, 12(5), e0178272.
Zheng et al., "Tertiary Structural Propensities Reveal Fundamental Sequence/Structure Relationships," Structure, May 5, 2015, 23(5), 961-971.
U.S. Appl. No. 12/525,123, filed Mar. 18, 2010, Bernal et al.
Bechara & Sagan, "Cell-penetrating peptides: 20 years later, where do we stand?," FEBS Lett., 2013, 587(12):1693-1702.
Bird et al., "Synthesis and Biophysical Characterization of Stabilized a-Helices of BCL-2 Domains," Methods in Enzymol, 2008, 446:369-386.
Computational Design of Ligand Binding Proteins, 2016, Chapter 14, 15 pages.
Czabotar et al.,"MutationtoBaxbeyondtheBH3DomainDisrupts InteractionswithPro-survivalProteinsandPromotesApoptosis," J. Biol. Chem., 2011, 286:7123-7131.
DeBartolo et al., "Genome-Wide Prediction and Validation of Peptides That Bind Human Prosurvival Bcl-2 Proteins," PLoS Computational Biol., 2014, 12 pages.
Devi et al., "Antibodies to poly[(2->8)-a-N-acelylneuraminic acid] and poly[(2->9)a-N-acetylneuraminic acid] are elicited by immunization of mice with *Escherichia coli* K92 conjugates: Potential vaccines for groups B and C meningococci and *E. coli* K1," Proc. Natl. Acad. Sci. USA, Aug. 1991, 88:7175-7179.
Fattom et al, "Serum Antibody Response in Adult Volunteers Elicited by Injection of *Streptococus pneumoniae* Type 12F Polysaccharide Alone or Conjugated to Diptheria Toxoid," Infect. Immun., Jul. 1990, 58:2309-2312.
Foight et al, "Designed BH3 Peptides with High Affinity and Specificity for Targeting Mcl-1 in Cells," ACS Chem., 2014, Biol. 9:1962-1968.
Foight et al, "Enriching peptide libraries for binding affinity and specificity through computationally directed library design," Methods Mol. Biol., 2014, 1561:213-232.
Gietz et al, "Transformation of yeast by lithium acetate/single-stranded carrier DNA/polyethylene glycol method." Methods Enzymol, 2002, 350:87-96.
Herman et al, "Completing the family portrait of the anti-apoptotic Bcl-2 proteins: Crystal structure of human Bfl-1 in complex withBim," FEBS Lett, 2008, 582:3590-3594.
Koss et al, "Defining specificity and on-target activity of BH3-mimetics using engineered B-ALL cell lines," Oncotarget, 2016, 7:11500-11511.

(56) References Cited

OTHER PUBLICATIONS

Lee et al, "ConformationalChangesinBcl-2Pro-survivalProteins DetermineTheirCapacitytoBindLigands," J. Biol. Chem., 2009, 284:30508-30517.

PCT International Search Report and Written Opinion in International Appln. No. PCT/US2017/43219, dated Jan. 8, 2018, 14 pages.

Qian et al, "Discovery and Mechanism of Highly Efficient Cyclic Cell-Penetrating Peptides," Biochem., 2016, 55(18):2601-2612.

Roehrl et al, "A General Framework for Development and Data Analysis of Competitive High-Throughput Screens for Small-Molecule Inhibitors of Protein-Protein Interactions by Fluorescence Polarization," Biochemistiy, 2004, 43:16056-16066.

Ryan et al., "iBH3: simple, fixable BH3 profiling to determine apoptotic priming in primary tissue by flow cytometr," Biol. Chem., 2016, 397:671-678.

Schafmeister et al, "An All-Hydrocarbon Cross-Linking System for Enhancing the Helicity and Metabolic Stability of Peptides," J. Am. Chem. Soc., 2000, 122:5891-5892.

Shannon & Weerapana, "Covalent protein modification: the current landscape of residue-specific electrophiles," Curr, Opin. Chem. Biol., 2015, 24, 18-26.

Stebbins et al. "Structure-based design of covalent Siah inhibitors." Chem Biol., Aug. 22, 2013, 20(8):973-82.

Szu et al, "Comparative Immunogenicities of Vi Polysaccharide-Protein Conjugates Composed of Cholera Toxin or Its B Subunit as a Carrier Bound to High- or Lower-Molecular-Weight Vi," Infect. Immun., Dec. 1989, 57:3823-3827.

Szu et al, "Laboratory and Preliminary Clinical Characterization of Vi Capsular Polysaccharide-Protein Conjugate Vaccines," Infect. Immun., 1994, 62:4440-4444.

Szu et al, "Vi Capsular Polysaccharide-Protein Conjugates For Prevention of Typhoid Fever," J. Exp. Med., Nov. 1, 1987, 166:1510-1524.

Szu et al., "Relation between Structure and Immunologic Properties of the Vi Capsular Polysaccharide," Infect. Immun., Sep. 7, 1991, 59:4555-4561.

Walensky et al, Activation of Apoptosis in Vivo by a Hydrocarbon-Stapled BH3 Helix, Science, Sep. 3, 2004, 305:1466-1470.

Wilen et al, "Strategies in Optical Resolutions," Tetrahedron, 1977, 33:2725-2736.

* cited by examiner

```
            |-|- - - 2 - - -|- - - 3 - - -|- - - 4 - - -|
             g a b c d e f g a b c d e f g a b c d e f g
Puma BH3:    W A R E I G A Q L R R M A D D L N A Q Y E R
             E       A   C       A     E A       A
             I       C   D       C     H D       F
             K       D   F       F     I F       I
             L       S   G       G     K H       L
             P       Y   H       I     L I       P
             Q           I       L     M N       S
             T           L       P     N P       T
             V           N       R     Q S       V
                         R       S     V T
                         S       T       V
                         V       V       Y
                         Y
```

```
        - -|- - -2- - -|- - -3- - -|- - -4- - -|
          f g a b c d e f g a b c d e f g a b c d e f g
PUM
 A      Q W A R E I G A Q L R R M A D D L N A Q Y E R
FS1     Q W V R E I A A G L R L A A D N V N A Q L E R
FS2     Q W V R E I A A G L R R A A D D V N A Q V E R
FS3     Q W I R E I A A G L R R E A D I L N A Q V E R
          increase size        decrease size
``` log PE fluorescence (binding)

log APC fluorescence (expression)

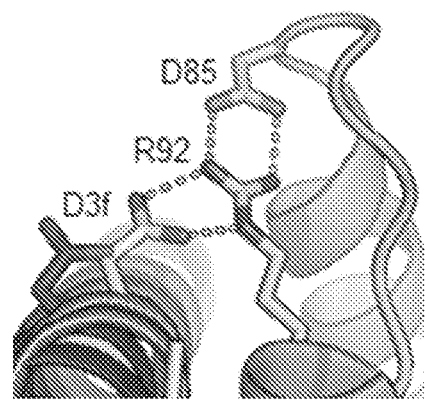
FIG. 5C
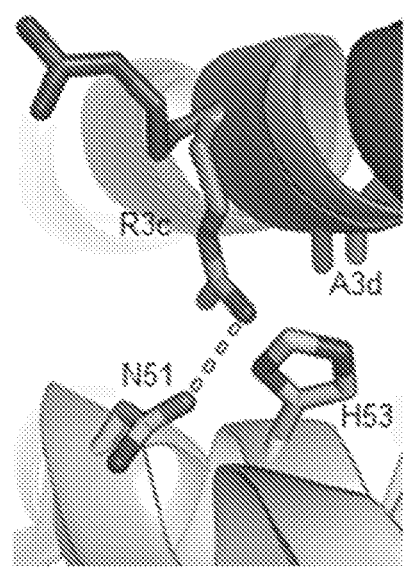 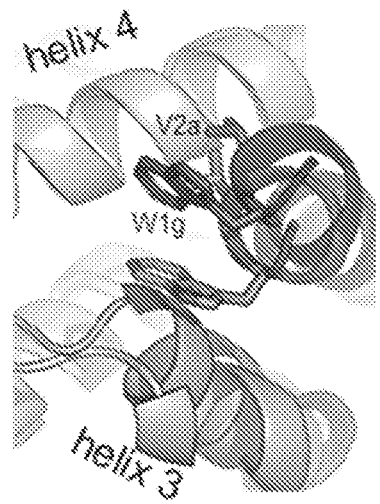
FIG. 5D          FIG. 5E

| Peptide | Sequence fgabcdefgabcdefgabcdefgabcdefg | Ki (nM) | | | | |
|---|---|---|---|---|---|---|
| | | Bfl-1 | Mcl-1 | Bcl-xl | Bcl-w | Bcl-2 |
| Puma | QWAREIGAQLRRMADDLNAQYER | 5.1±1.1 | 2.7±1.1 | 3.2±1.3 | 6.0±3.5 | 6.8±2.7 |
| FS1 | QWVREIAAGLRLAADNVNAQLER | 16.4±8 | >5000 | 2724±713 | 8880±3483 | 6940±2841 |
| FS2 | QWVREIAAGLRRAADVNAQVER | 24.8±1 | 2583±794 | 7337±2188 | 7214±1245 | 2450±141 |
| FS3 | QWIREIAAGLRRFADILNAQVER | 2.1±.3 | 711±81 | 105±3 | 828±138 | 2362±368 |

FIG. 6

|        | Bcl-2 | Bcl-xl | Bcl-W | Bfl-1 | Mcl-1 |
|--------|-------|--------|-------|-------|-------|
| Puma   | 6.8   | 3.2    | 6     | 5.1   | 2.7   |
| Puma Y4eV | 16 | 4.7    | 11    | 23    | 60    |
| FS2    | 2450  | 7337   | 7214  | 24.8  | 2583  |
| FS2 V4eY | 1000 | 1379  | 1974  | 9.3   | 85.22 |

```
     Puma      QWAREIGAQLRRMADDLNAQYER
Puma Y4eV      QWAREIGAQLRRMADDLNAQVER
      FS2      QWVREIAAGLRRAADDVNAQVER
 FS2 Y4eV      QWVREIAAGLRRAADDVNAQYER
```

FIG. 7

|        | Bcl-2 | Bcl-xl | Bcl-W | Bfl-1 | Mcl-1 |
|--------|-------|--------|-------|-------|-------|
| Puma   | 6.8   | 3.2    | 6     | 5.1   | 2.7   |
| Puma 2a 2e | 40.3 | 8   | 5     | 3     | 0.5   |
| Fs2 2a 2e | 7350 | 10444 | 10000 | 820  | 10000 |
| FS2    | 2450  | 7337   | 7214  | 24.8  | 2583  |

```
         Puma      QWAREIGAQLRRMADDLNAQYER
Puma A2aV G2eA     QWVREIAAQLRRMADDLNAQYER
 FS2 V2aA A2eG     QWAREIGAGLRRAADDVNAQVER
          FS2      QWVREIAAGLRRAADDVNAQVER
```

FIG. 8

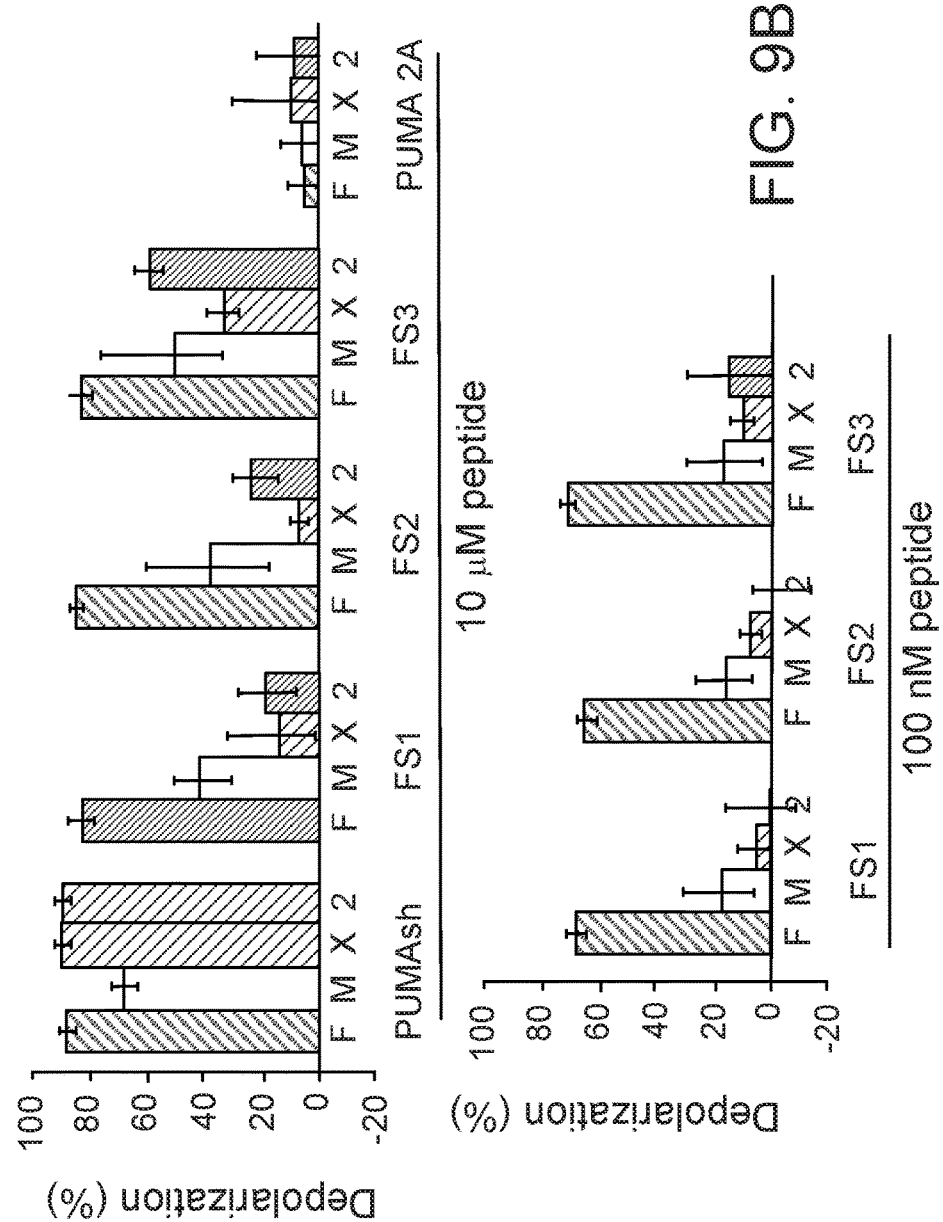

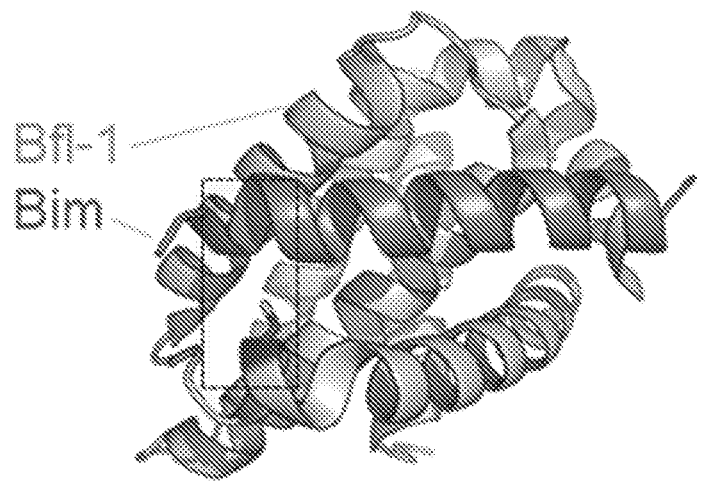
FIG. 10A
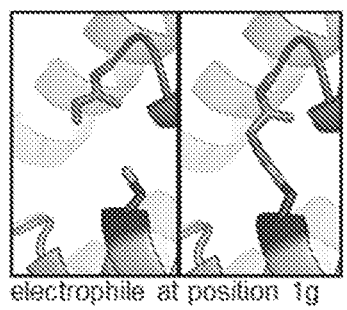 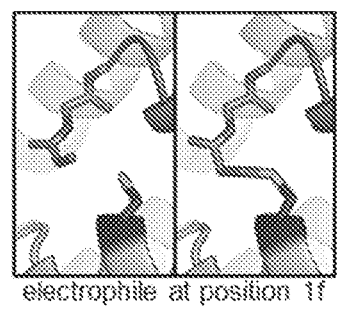
FIG. 10B      FIG. 10C

| Peptide | Sequence ----2-------3------4--- fgabcdefgabcedfgabcdefg |
|---|---|
| Puma | QWAREIGAQLRRMADDLNAQYER |
| FS1 | QWVREIAAGLRLAADNVNAQLER |
| FS2 | QWVREIAAGLRRAADDVNAQVER |
| FS3 | QWIREIAAGLRRFADILNAQVER |
| FS2X | 1VREIAAGLRRAADDVNAQVER |
| FS2gX | 1GVREIAYGLRRAADDVNAQVER |
| FS2gXH | 1GVRHIAYGLRRAADDVNAQVER |
| FS2gXHD | 1GVRHIAYDLRRAADDVNAQVER |
| FS2gXHE | 1GVRHIAYELRRAADDVNAQVER |
| FS2gXDap | 1GVR2IAYGLRRAADDVNAQVER |
| FS2gXDap | 1GVRE3AYGLRRAADDVNAQVER |
| FS2gAc | GVREIAYGLRRAADDVNAQVER |

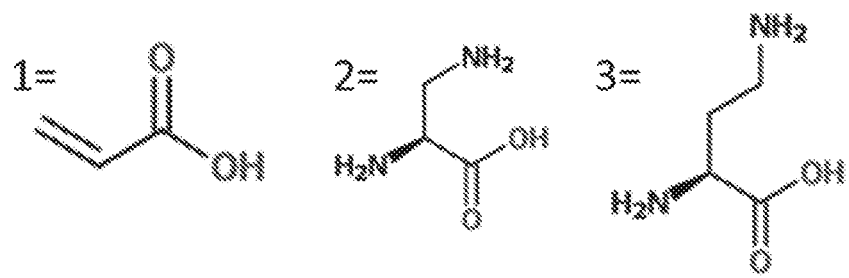

FIG. 11

SEQUENCE LISTING

```
<160> NUMBER OF SEQ ID NOS: 34

<210> SEQ ID NO 1
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Q or a conservative substitution, or not
      present
<220> FEATURE:
<221> NAME/KEY: MOD_RES
<222> LOCATION: (2)..(2)
<223> OTHER INFORMATION: W or a conservative substitution, G or a
      conservative substitution, 4, 4-biphenylalanine, azidoalanine,
      or not present
```

```
<220> FEATURE:
<221> NAME/KEY: MOD_RES
<222> LOCATION: (3)..(3)
<223> OTHER INFORMATION: A or a conservative substitution, V or a
      conservative substitution, or I or a conservative substitution
<220> FEATURE:
<221> NAME/KEY: MOD_RES
<222> LOCATION: (4)..(4)
<223> OTHER INFORMATION: R or a conservative substitution
<220> FEATURE:
<221> NAME/KEY: MOD_RES
<222> LOCATION: (5)..(5)
<223> OTHER INFORMATION: E or a conservative substitution, H or a
      conservative substitution, or 2,3-diaminopropanoic acid
<220> FEATURE:
<221> NAME/KEY: MOD_RES
<222> LOCATION: (6)..(6)
<223> OTHER INFORMATION: I or a conservative substitution, norleucine,
      homoleucine, cyclohexylalanine, 2-aminoheptanoic acid, or
      2,4-diaminobutyric acid
<220> FEATURE:
<221> NAME/KEY: MOD_RES
<222> LOCATION: (7)..(7)
<223> OTHER INFORMATION: G or a conservative substitution, or A or a
      conservative substitution
<220> FEATURE:
<221> NAME/KEY: MOD_RES
<222> LOCATION: (8)..(8)
<223> OTHER INFORMATION: A or a conservative substitution, or Y or a
      conservative substitution
<220> FEATURE:
<221> NAME/KEY: MOD_RES
<222> LOCATION: (9)..(9)
<223> OTHER INFORMATION: Q or a conservative substitution, G or a
      conservative substitution, D or a conservative substitution, or
      E or a conservative substitution
<220> FEATURE:
<221> NAME/KEY: MOD_RES
<222> LOCATION: (10)..(10)
<223> OTHER INFORMATION: L or a conservative substitution,
      cyclohexylalanine, or homoleucine
<220> FEATURE:
<221> NAME/KEY: MOD_RES
<222> LOCATION: (11)..(11)
<223> OTHER INFORMATION: R or a conservative substitution
<220> FEATURE:
<221> NAME/KEY: MOD_RES
<222> LOCATION: (12)..(12)
<223> OTHER INFORMATION: R or a conservative substitution, or L or a
      conservative substitution
<220> FEATURE:
<221> NAME/KEY: MOD_RES
<222> LOCATION: (13)..(13)
<223> OTHER INFORMATION: M or a conservative substitution, A or a
      conservative substitution, F or a conservative substitution,
      d-phenylglycine, d-histidine, d-leucine, alpha-aminoisobutyric
      acid, or cyclohexanecarboxylic acid
<220> FEATURE:
<221> NAME/KEY: MOD_RES
<222> LOCATION: (14)..(14)
<223> OTHER INFORMATION: A or a conservative substitution, ornithine,
      2,4-diaminobutyric acid, or 2,3-diaminopropanoic acid
<220> FEATURE:
<221> NAME/KEY: MOD_RES
<222> LOCATION: (15)..(15)
<223> OTHER INFORMATION: D or a conservative substitution, or
      homoglutamate
<220> FEATURE:
<221> NAME/KEY: MOD_RES
<222> LOCATION: (16)..(16)
<223> OTHER INFORMATION: D or a conservative substitution, N or a
      conservative substitution, or I or a conservative substitution
<220> FEATURE:
<221> NAME/KEY: MOD_RES
<222> LOCATION: (17)..(17)
<223> OTHER INFORMATION: L or a conservative substitution, V or a
      conservative substitution, or d-cyclohexylalanine
```

```
<220> FEATURE:
<221> NAME/KEY: MOD_RES
<222> LOCATION: (18)..(18)
<223> OTHER INFORMATION: N or a conservative substitution
<220> FEATURE:
<221> NAME/KEY: MOD_RES
<222> LOCATION: (19)..(19)
<223> OTHER INFORMATION: A or a conservative substitution
<220> FEATURE:
<221> NAME/KEY: MOD_RES
<222> LOCATION: (20)..(20)
<223> OTHER INFORMATION: Q or a conservative substitution
<220> FEATURE:
<221> NAME/KEY: MOD_RES
<222> LOCATION: (21)..(21)
<223> OTHER INFORMATION: Y or a conservative substitution, L or a
      conservative substitution, or V or a conservative substitution
<220> FEATURE:
<221> NAME/KEY: MOD_RES
<222> LOCATION: (22)..(22)
<223> OTHER INFORMATION: E or a conservative substitution
<220> FEATURE:
<221> NAME/KEY: MOD_RES
<222> LOCATION: (23)..(23)
<223> OTHER INFORMATION: R or a conservative substitution
<220> FEATURE:
<223> OTHER INFORMATION: See specification as filed for detailed
      description of substitutions and preferred embodiments

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 2
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gln Trp Val Arg Glu Ile Ala Ala Gly Leu Arg Leu Ala Ala Asp Asn
1               5                   10                  15

Val Asn Ala Gln Leu Glu Arg
            20

<210> SEQ ID NO 3
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Trp Val Arg Glu Ile Ala Ala Gly Leu Arg Arg Ala Ala Asp Asp
1               5                   10                  15

Val Asn Ala Gln Val Glu Arg
            20

<210> SEQ ID NO 4
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 4

Gln Trp Ile Arg Glu Ile Ala Ala Gly Leu Arg Arg Phe Ala Asp Ile
1               5                   10                  15

Leu Asn Ala Gln Val Glu Arg
            20

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Val Arg Glu Ile Ala Tyr Gly Leu Arg Arg Ala Ala Asp Asp Val Asn
1               5                   10                  15

Ala Gln Val Glu Arg
            20

<210> SEQ ID NO 6
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Trp Ala Arg Glu Ile Gly Ala Gln Leu Arg Arg Met Ala Asp Asp
1               5                   10                  15

Leu Asn Ala Gln Val Glu Arg
            20

<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Trp Val Arg Glu Ile Ala Ala Gly Leu Arg Arg Ala Ala Asp Asp
1               5                   10                  15

Val Asn Ala Gln Tyr Glu Arg
            20

<210> SEQ ID NO 8
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Trp Val Arg Glu Ile Ala Ala Gln Leu Arg Arg Met Ala Asp Asp
1               5                   10                  15

Leu Asn Ala Gln Tyr Glu Arg
            20
```

```
<210> SEQ ID NO 9
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Trp Ala Arg Glu Ile Gly Ala Gly Leu Arg Arg Ala Ala Asp Asp
1               5                   10                  15

Val Asn Ala Gln Val Glu Arg
            20

<210> SEQ ID NO 10
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Val Arg Glu Ile Ala Tyr Gly Leu Arg Arg Ala Ala Asp Asp Val
1               5                   10                  15

Asn Ala Gln Val Glu Arg
            20

<210> SEQ ID NO 11
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Val Arg His Ile Ala Tyr Gly Leu Arg Arg Ala Ala Asp Asp Val
1               5                   10                  15

Asn Ala Gln Val Glu Arg
            20

<210> SEQ ID NO 12
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Val Arg His Ile Ala Tyr Asp Leu Arg Arg Ala Ala Asp Asp Val
1               5                   10                  15

Asn Ala Gln Val Glu Arg
            20

<210> SEQ ID NO 13
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 13

Gly Val Arg His Ile Ala Tyr Glu Leu Arg Arg Ala Ala Asp Asp Val
1               5                   10                  15

Asn Ala Gln Val Glu Arg
            20

<210> SEQ ID NO 14
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: 2,3-diaminopropanoic acid

<400> SEQUENCE: 14

Gly Val Arg Xaa Ile Ala Tyr Gly Leu Arg Arg Ala Ala Asp Asp Val
1               5                   10                  15

Asn Ala Gln Val Glu Arg
            20

<210> SEQ ID NO 15
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 2,4-diaminobutyric acid

<400> SEQUENCE: 15

Gly Val Arg Glu Xaa Ala Tyr Gly Leu Arg Arg Ala Ala Asp Asp Val
1               5                   10                  15

Asn Ala Gln Val Glu Arg
            20

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Arg Lys Lys Arg Arg Gln Arg Arg Arg Pro Pro Gln
1               5                   10

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Leu Ile Ile Leu Arg Arg Arg Ile Arg Lys Gln Ala His Ala His
1               5                   10                  15

Ser Lys

```
<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Glu Thr Trp Trp Glu Thr Trp Trp Thr Glu Trp Ser Gln Pro Lys
1               5                  10                  15

Lys Lys Arg Lys Val
            20

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Gln Ile Lys Ile Trp Phe Gln Asn Arg Arg Met Lys Trp Lys Lys
1               5                  10                  15

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(11)
<223> OTHER INFORMATION: This sequence may encompass 7 to 11 residues

<400> SEQUENCE: 20

Arg Arg Arg Arg Arg Arg Arg Arg Arg Arg Arg
1               5                  10

<210> SEQ ID NO 21
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Trp Thr Leu Asn Ser Ala Gly Tyr Leu Leu Gly Lys Ile Asn Leu
1               5                  10                  15

Lys Ala Leu Ala Ala Leu Ala Lys Lys Ile Leu
            20                  25

<210> SEQ ID NO 22
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 22

Gly Ala Leu Phe Leu Gly Phe Leu Gly Ala Ala Gly Ser Thr Met Gly
1               5                   10                  15

Ala Trp Ser Gln Pro Lys Lys Arg Lys Val
            20                  25

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Leu Ala Leu Lys Leu Ala Leu Lys Ala Leu Lys Ala Ala Leu Lys
1               5                   10                  15

Leu Ala

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Arg Trp Trp Arg Arg Trp Arg Arg
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Cys Tyr Gly Gly Arg Gly Asp Thr Pro
1               5

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Trp Ile Ala Gln Glu Leu Arg Arg Ile Gly Asp Glu Phe Asn Ala
1               5                   10                  15

Tyr Tyr

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 27

Gly Gly Gly Gly Ser Gly Gly Gly Gly Ser Gly Gly Gly Gly Ser
1               5                   10                  15

<210> SEQ ID NO 28
<211> LENGTH: 98
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(38)
<223> OTHER INFORMATION: a, c, t, g, unknown or other
<220> FEATURE:
<221> NAME/KEY: modified_base
<222> LOCATION: (50)..(50)
<223> OTHER INFORMATION: a, c, t, g, unknown or other
<220> FEATURE:
<221> NAME/KEY: modified_base
<222> LOCATION: (62)..(62)
<223> OTHER INFORMATION: a, c, t, g, unknown or other
<220> FEATURE:
<221> NAME/KEY: modified_base
<222> LOCATION: (74)..(74)
<223> OTHER INFORMATION: a, c, t, g, unknown or other

<400> SEQUENCE: 28
cggatccggt ggccaatggv hacgtgaaat tkvtgccndc ctgcgtcgcn bcgcggatvw       60
knhtaatgcc caanytgaac gtcgtcgcca ggaggaac                              98

<210> SEQ ID NO 29
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cgccttgttc ctcctggcga cgacgttcat attgggc                              37

<210> SEQ ID NO 30
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A, E, I, K, L, P, Q, T or V
<220> FEATURE:
<221> NAME/KEY: MOD_RES
<222> LOCATION: (6)..(6)
<223> OTHER INFORMATION: G, A, C, D, S or Y
<220> FEATURE:
<221> NAME/KEY: MOD_RES
<222> LOCATION: (8)..(8)
<223> OTHER INFORMATION: Q, C, D, F, G, H, I, L, N, R, S, V or Y
<220> FEATURE:
<221> NAME/KEY: MOD_RES
<222> LOCATION: (12)..(12)
<223> OTHER INFORMATION: M, A, C, F, G, I, L, P, R, S, T or V
<220> FEATURE:
<221> NAME/KEY: MOD_RES
<222> LOCATION: (15)..(15)
<223> OTHER INFORMATION: D, E, H, I, K, L, M, N, Q or V

```
<220> FEATURE:
<221> NAME/KEY: MOD_RES
<222> LOCATION: (16)..(16)
<223> OTHER INFORMATION: L, A, D, F, H, I, N, P, S, T, V or Y
<220> FEATURE:
<221> NAME/KEY: MOD_RES
<222> LOCATION: (20)..(20)
<223> OTHER INFORMATION: Y, A, F, I, L, P, S, T or V

<400> SEQUENCE: 30

Trp Xaa Arg Glu Ile Xaa Ala Xaa Leu Arg Arg Xaa Ala Asp Xaa Xaa
1               5                   10                  15

Asn Ala Gln Xaa Glu Arg
            20

<210> SEQ ID NO 31
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Trp Ala Arg Glu Ile Gly Ala Gln Leu Arg Arg Met Ala Asp Asp
1               5                   10                  15

Leu Asn Ala Gln Tyr Glu Arg
            20

<210> SEQ ID NO 32
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Trp Ala Arg Glu Ile Gly Ala Gln Leu Arg Arg Met Ala Asp Asp
1               5                   10                  15

Leu Asn Ala Gln Tyr Glu
            20

<210> SEQ ID NO 33
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Trp Val Arg Glu Ile Ala Ala Gly Leu Arg Arg Ala Ala Asp Asp
1               5                   10                  15

Val Asn Ala Gln Val Glu
            20

<210> SEQ ID NO 34
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 34

Val Arg Glu Ile Ala Ala Gly Leu Arg Arg Ala Ala Asp Asp Val Asn
1               5                   10                  15

Ala Gln Val Glu Arg
            20
```

SELECTIVE BFL-1 PEPTIDES

CLAIM OF PRIORITY

This application is a § 371 National Stage Application of PCT/US2017/043219, filed Jul. 21, 2017, which claims the benefit of U.S. Provisional Patent Application No. 62/365,484, filed on Jul. 22, 2016, and U.S. Provisional Patent Application No. 61/517,146, filed on Jun. 8, 2017. The entire contents of the foregoing are hereby incorporated by reference in the present application.

FEDERALLY SPONSORED RESEARCH OR DEVELOPMENT

This invention was made with Government support under Grant No. 5-R01 GM110048-03 awarded by the National Institutes of Health and by the National Science Foundation Graduate Research Fellowship under primary award number 1122374. The Government has certain rights in the invention.

TECHNICAL FIELD

This disclosure relates to peptides that bind Bfl-1 and methods of using such peptides in the treatment and diagnosis of cancer.

BACKGROUND

Bfl-1 is an anti-apoptotic protein that regulates commitment to the mitochondrial pathway of apoptosis and plays a critical role in tumor cells survival and the chemotherapy resistance of many human cancers. Bfl-1 and other members of the Bcl-2 family (e.g., Bcl-$x_L$, Bcl-2, Bcl-w, Mcl-1, and Bcl-b) block apoptosis by interfering with the homo-oligomerization of Bak and Bax. The anti-apoptotic proteins either bind directly to Bax or Bak or bind related pro-apoptotic activator proteins (Bim, Bid, and Puma), preventing activation of Bax and Bak. Other proteins having BH3-domains, called sensitizers, antagonize anti-apoptotic function by binding competitively with Bax/Bak and activators.

Agents that selectively bind Bfl-1 compared to other members of the anti-apoptotic Bcl-2 family proteins, such as Bcl-$x_L$, Bcl-2, or Mcl-1, may be useful in treating a variety of cancers.

SUMMARY

The present disclosure describes peptides that mimic the BH3 motif of human PUMA protein and bind human Bfl-1, inhibiting its function. The peptides are relatively selective for binding Bfl-1 in that they bind human Bfl-1 with greater affinity than they bind one or more of several proteins considered human homologs of Bfl-1, for example, Bcl-1, Bcl-w, Bcl-$x_L$, and Bcl-2.

In some aspects, the present disclosure provides a compound comprising, consisting essentially of, or consisting of a polypeptide comprising the amino acid sequence: F1 G1 A2 B2 C2 D2 E2 F2 G2 A3 B3 C3 D3 E3 F3 G3 A4 B4 C4 D4 E4 F4 G4 (SEQ ID NO:1), wherein F1 is Q or a conservative substitution, or is missing; G1 is W or a conservative substitution, G or a conservative substitution, 4,4-biphenylalanine, azidoalanine, or is missing; A2 is A or a conservative substitution, V or a conservative substitution, I or a conservative substitution; B2 is R or a conservative substitution; C2 is E or a conservative substitution, H or a conservative substitution, or 2,3-diaminopropanoic acid; D2 is I or a conservative substitution, norleucine, homoleucine, cyclohexylalanine, 2-aminoheptanoic acid, or 2,4-diaminobutyric acid; E2 is G or a conservative substitution, A or a conservative substitution; F2 is A or a conservative substitution, Y or a conservative substitution; G2 is Q or a conservative substitution, G or a conservative substitution, D or a conservative substitution, E or a conservative substitution; A3 is L or a conservative substitution, cyclohexylalanine, or homoleucine; B3 is R or a conservative substitution; C3 is R or a conservative substitution, L or a conservative substitution; D3 is M or a conservative substitution, A or a conservative substitution, F or a conservative substitution, d-phenylglycine, d-histidine, d-leucine, α-aminoisobutyric acid, or cyclohexanecarboxylic acid; E3 is A or a conservative substitution, ornithine, 2,4-diaminobutyric acid, or 2,3-diaminopropanoic acid; F3 is D or a conservative substitution, or homoglutamate; G3 is D or a conservative substitution, N or a conservative substitution, I or a conservative substitution; A4 is L or a conservative substitution, V or a conservative substitution, or d-cyclohexylalanine; B4 is N or a conservative substitution; C4 is A or a conservative substitution; D4 is Q or a conservative substitution; E4 is Y or a conservative substitution, L or a conservative substitution, V or a conservative substitution; F4 is E or a conservative substitution; G4 is R or a conservative substitution; provided that A2, E2, G2, C3, D3, G3, A4 and E4 are not A, Q Q, R, M, D, L and Y respectively. In some embodiments, F1 is Q or is missing; G1 is W, Q or is missing; A2 is V or I; B2 is R; C2 is E, H, or 2,3-diaminopropanoic acid; D2 is I or 2,4-diaminobutyric acid; E2 is A; F2 is A or Y; G2 is G D, or E; A3 is L; B3 is R; C3 is L or R; D3 is A or F; E3 is A; F3 is D; G3 is N, D or I; A4 is L or V; B4 is N; C4 is A; D4 is Q; E4 is L or V; F4 is E; and G4 is R.

In some embodiments, an electrophilic group is attached to the N-terminus of the polypeptide via an amide bond. In some cases, the electrophilic group is an acrylamide.

In some embodiments, a cell penetrating peptide tag or an affinity tag is attached to the polypeptide. In some embodiments, the cell penetrating peptide tag or the affinity tag is attached to the N-terminus of the polypeptide. In some embodiments, the cell penetrating peptide tag or the affinity tag is attached to the C-terminus of the polypeptide. In some embodiments, the cell penetrating peptide tag is selected from the group consisting of a TAT peptide, a pVEC peptide, a Pep-1 peptide, a penetratin peptide, a polyarginine peptide, an FGF4-derived peptide, a transportan peptide, an MPG peptide, a MAP peptide, an RGW3 peptide, a CPP9 peptide, and a CPP12 peptide. In some embodiments, the affinity tag is selected from the group consisting of an AviTag, a Flag-tag, an HA-tag, a His-tag, a Myc-tag, an S-tag, a V5-tag, and a VSV-tag.

In various embodiments, A2 is V, E2 is A, G2 is G C3 is L, D3 is A, G3 is N, A4 is V and E4 is L. In some instances, A2 is V, E2 is A, G2 is G D3 is A, A4 is V and E4 is V. In some cases, A2 is I, E2 is A, G2 is G D3 is F, G3 is I and E4 is V.

In some embodiments, the compound includes the amino acid sequence: QWVREIAAGLRLAADNVAQLER (SEQ ID NO: 2), wherein up to 6 of the amino acids are substituted by another amino acid. In some embodiments, the compound includes the amino acid sequence: QWVRE-IAAGLRRAADDVNAQVER (SEQ ID NO:3), wherein up to 6 of the amino acids are substituted by another amino acid. In some embodiments, the compound includes the amino acid sequence: QWIREIAAGLRRFADILNAQVER (SEQ ID NO:4), wherein up to 6 of the amino acids are substituted by another amino acid. In some embodiments, the compound includes the amino acid sequence: VRE-IAYGLRRAADDVNAQVER (SEQ ID NO:5), wherein up to 6 of the amino acids are substituted by another amino acid. In some cases, an acrylamide is attached to the amino terminus of the polypeptide via an amide bond.

In another aspect, the present disclosure provides a compound comprising a polypeptide comprising an amino acid sequence selected from:

```
                              (SEQ ID NO: 6)
QWAREIGAQLRRNIADDLNAQVER;

(SEQ ID NO: 7)
QWVREIAAGLRRAADDVNAQYER;

(SEQ ID NO: 8)
QWVREIAAQLRRNIADDLNAQYER;

(SEQ ID NO: 9)
QWAREIGAGLRRAADDVNAQVER;

(SEQ ID NO: 10)
GVREIAYGLRRAADDVNAQVER;

(SEQ ID NO: 11)
GVREITAYGLRRAADDVNAQVER;

(SEQ ID NO: 12)
GVREITAYDLRRAADDVNAQVER;

(SEQ ID NO: 13)
GVREITAYELRRAADDVNAQVER;

(SEQ ID NO: 14)
GVR2IAYGLRRAADDVNAQVER;
and
                              (SEQ ID NO: 15)
GVRE3AYGLRRAADDVNAQVER;
``` wherein 2 is 2,3-diaminopropanoic acid, and 3 is 2,4-diaminobutyric acid. In some cases, the compound includes an electrophilic group attached to the N-terminus of the polypeptide via an amide bond. In some cases, the electrophilic group is an acrylamide.

In some cases, no more than 2 of the amino acids are replaced by another amino acid. In some instances, none of the amino acids are substituted by another amino acid.

In another aspect, the present disclosure provides a compound comprising a peptide comprising at least 16 contiguous amino acids of any of SEQ ID NOs: 1-15.

In some cases, the polypeptide portion of the compound consists of no more than 40, 35, 30, 25, 24, 23, 22, 21, 20, 19, 18, 17 or 16 amino acids or consists of 15-20, 15-25, 15-30 amino acids.

In another aspect, the present disclosure provides a pharmaceutical composition comprising a compound described herein. In some aspects, the present disclosure provides a pharmaceutical composition comprising at least one of the compounds described herein.

In another aspect, the present disclosure provides a method of treating cancer comprising administering a compound described herein.

In another aspect, the present disclosure provides a method of treating cancer comprising administering a pharmaceutical composition described herein.

In another aspect, the present disclosure provides a method for detecting a Bfl-1-dependent tumor cell, comprising: permeabilizing the tumor cell; contacting the tumor cell with any one of the compounds described herein; measuring the mitochondrial depolarization of the tumor cell; and detecting a Bfl-1-dependent tumor cell when the mitochondrial depolarization is increased as compared to a control tumor cell that has not been contacted by the compound.

In another aspect, the present disclosure provides a method of detecting Bfl-1-induced resistance to chemotherapeutics in a tumor cell, comprising: permeabilizing the tumor cell; contacting the tumor cell with any one of the compounds described herein; measuring the mitochondrial depolarization of the tumor cell; and detecting Bfl-1-induced resistance to chemotherapeutics when the mitochondrial depolarization is increased as compared to a control tumor cell that has not been contacted by the compound.

In another aspect, the present disclosure provides a method for detecting overexpression of Bfl-1 in a tumor cell, comprising: permeabilizing the tumor cell; contacting the tumor cell with any one of the compounds described herein; and measuring the mitochondrial depolarization of the tumor cell; and detecting overexpression of Bfl-1 when the mitochondrial depolarization is increased as compared to a control tumor cell that has not been contacted by the compound.

In another aspect, the present disclosure provides a method of treating cancer in a subject in need thereof, comprising administering a therapeutically effective amount of any one of the compounds described herein and a therapeutically effective amount of a chemotherapeutic agent. In various embodiments, the administering the therapeutically effective amount of the chemotherapeutic agent is performed before, after, or concurrently with the administering of the compound.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1A is a sequence logo of unique peptide sequences in the final sorted pool from the Bfl-1 targeted library. FIG. 1B is a diagram demonstrating point mutants in Puma BH3. Point mutations that were tested for their contribution to Bfl-1 selective binding are shown in bold. FIG. 1C shows the location of mutated sites in FS1, FS2, and FS3. Mutations at positions A2 and E2 are in bold and positions G2, D3, A4, and E4 are underlined. FIG. 1D depicts the structure of Bfl-1 (gray surface) bound to PUMA (dark gray) with side chains shown for positions A2, E2, G2, D3, A4, and E4. FIG. 1E depicts a diagram showing that the non-additive mutational energies for PUMA/FS2 chimeric proteins indicate coupling between N- and C-terminal mutations. Data are $K_i \pm SD$ of 3 or more independent fluorescence anisotropy competition experiments.

Figure 2A:
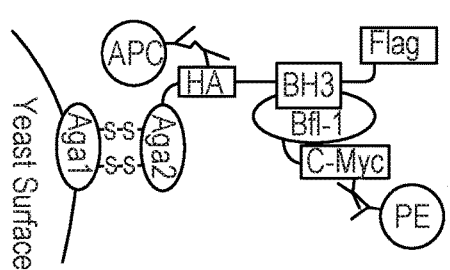
Figure 2B:
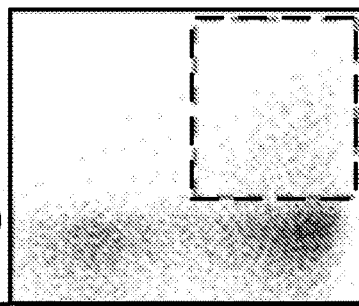
Figure 2C:
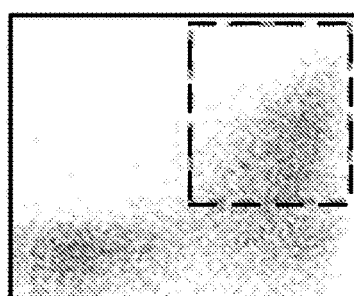
Figure 2D:
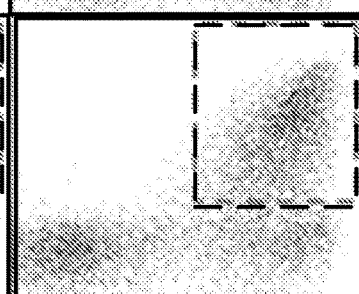
Figure 2E:
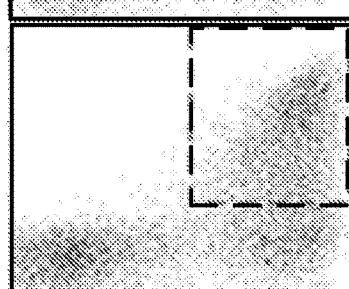
Figure 2F:
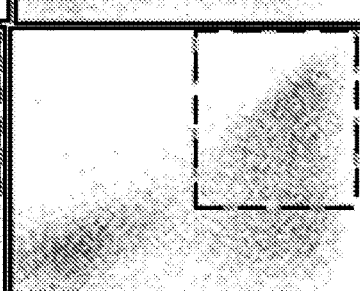
Figure 2G:
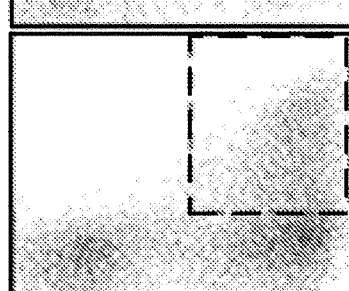
Figure 2H:
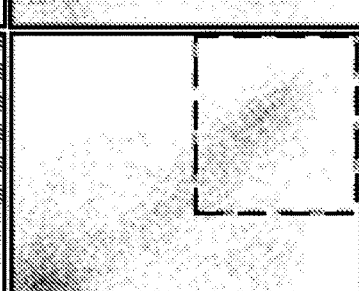
Figure 2I:
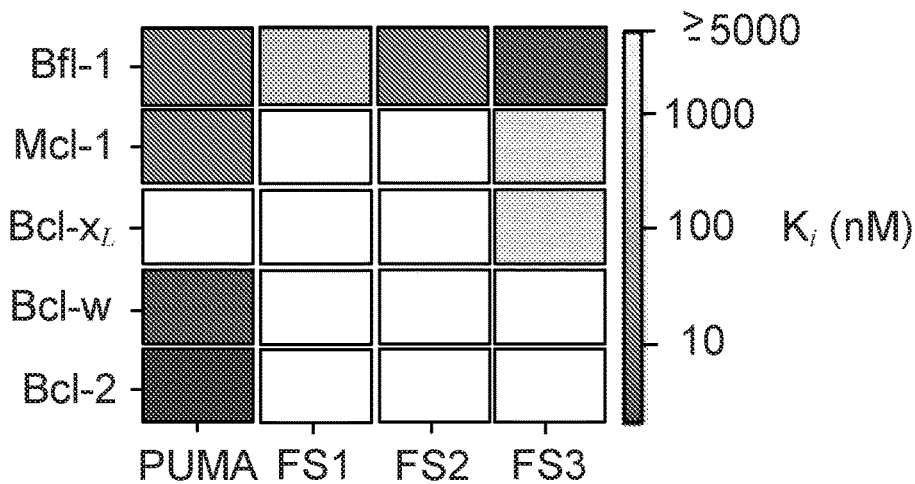

FIG. 2A-I describe experimental library screening for Bfl-1 affinity and selectivity. FIG. 2A is a diagram depicting yeast-surface display configuration. BH3 peptides were expressed as fusions to Aga2; HA tag expression was detected with APC and Bfl-1 binding was detected with PE. FIG. 2B shows that in FACS analysis, only ~5% of cells in the unsorted PUMA libraries bound to Bfl-1 at 100 nM. FIG. 2C shows library binding to 100 nM Bfl-1 after one round of enrichment. FIG. 2D shows library binding to Bcl-$x_L$, an off-target protein (100 nM), after one round of enrichment. FIG. 2E shows library binding to Bcl-2, an off-target protein (100 nM), after one round of enrichment. FIG. 2F shows library binding to Bcl-w, an off-target protein (100 nM), after one round of enrichment. FIG. 2G shows library binding to Mcl-1, an off-target protein (100 nM), after one round of enrichment. FIG. 2H shows library binding to 100 nM Myc-tagged Bfl-1 in the presence of excess unlabeled competitor (Mcl-1, Bcl-2, Bcl-w, and Bcl-$x_L$; 1 µM each) after six rounds of enrichment. FIG. 2I depicts inhibition constants determined using fluorescence anisotropy for 23-residue peptides corresponding to PUMA BH3, FS1, FS2 and FS3.

Figure 3A:
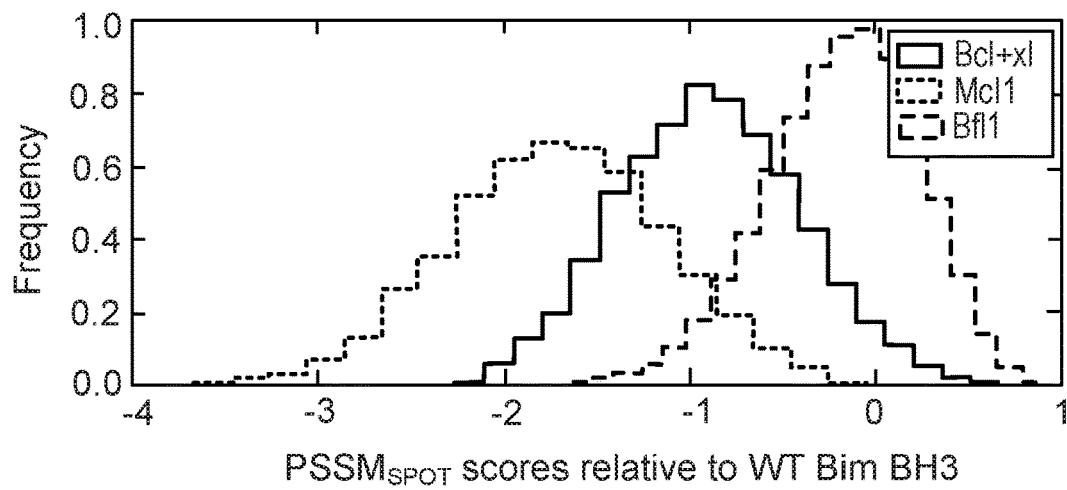
Figure 3B:
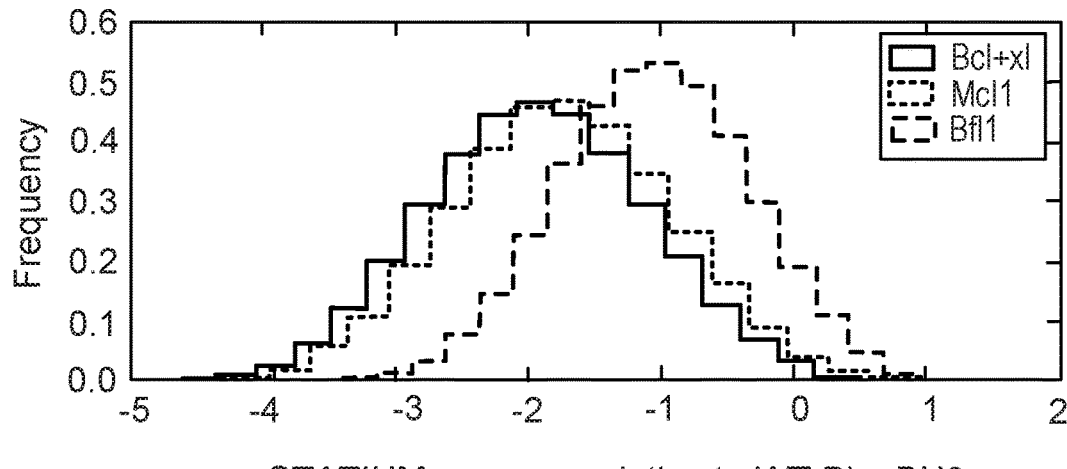

FIG. 3A-B are the results of the PSSM and STATIUM analysis of the yeast surface display library. The Puma BH3 library was evaluated using a PSSM (FIG. 3A) derived from SPOT array mutational data and with STATIUM (FIG. 3B) based on analysis of crystal structures of Bim bound to Bfl-1 (2VM6), Mcl-1 (2PQK), and Bcl-$x_L$ (3FDL).

Figure 4A:
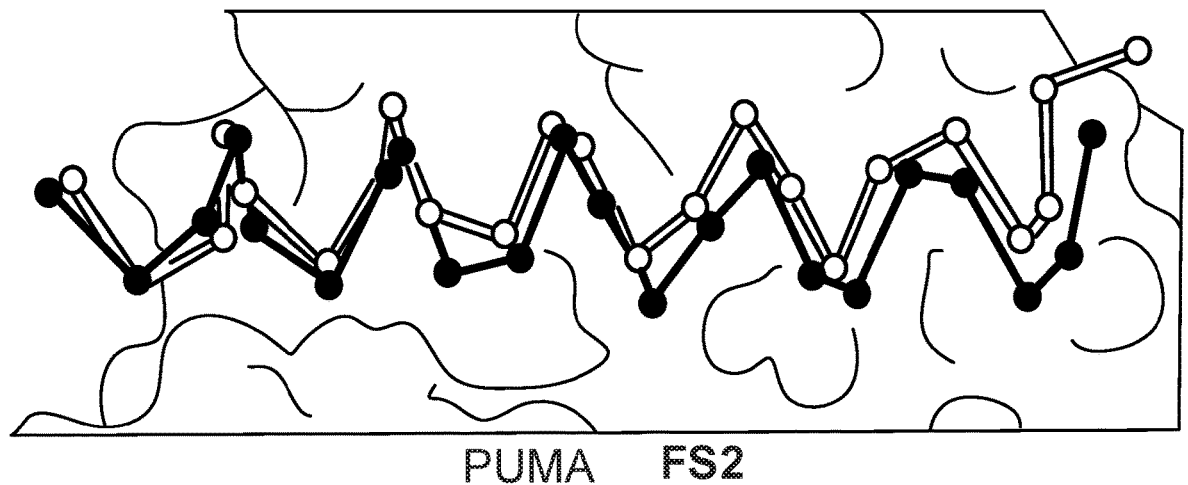
Figure 4B:
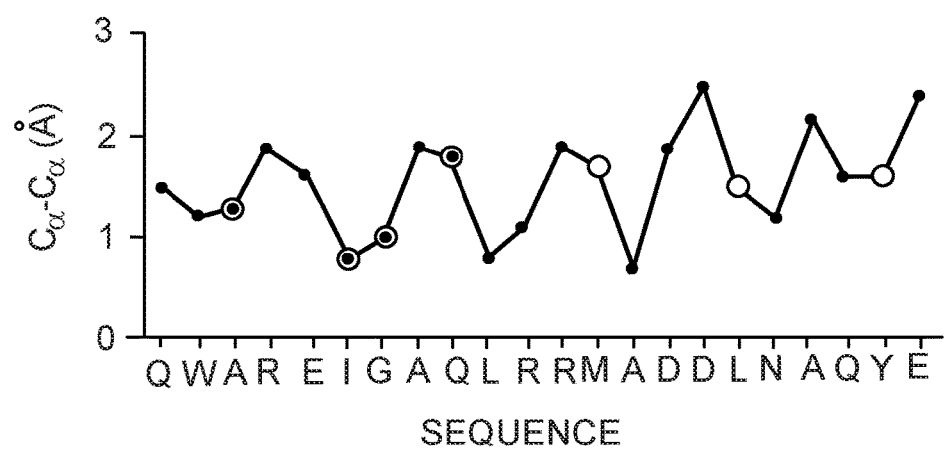
Figure 4C:
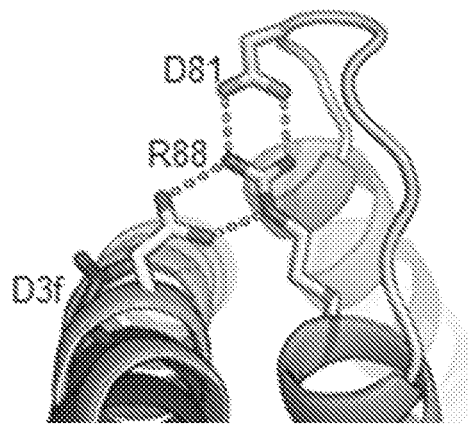
Figure 4D:
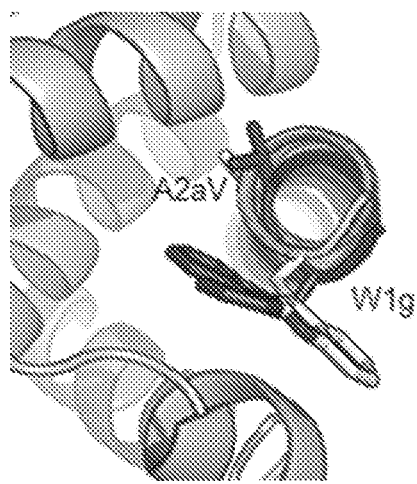
Figure 4E:
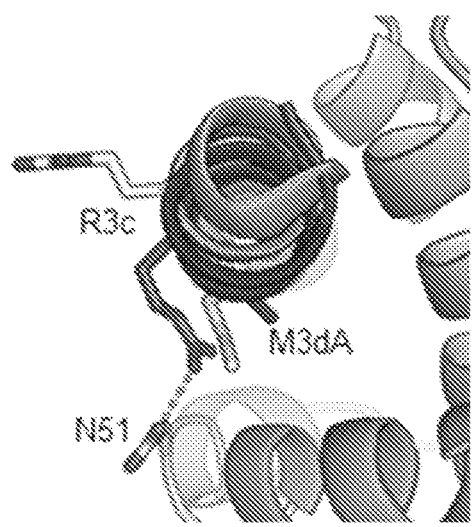

FIG. 4A-E depict high-resolution structures of PUMA and FS2 bound to human Bfl-1. FIG. 4A depicts a structure that shows the binding groove of Bfl-1 (gray, surface) with PUMA (light gray) and FS2 (dark gray). FIG. 4B depicts $C_\alpha$-$C_\alpha$ shifts between FS2 and PUMA. Sites with larger/smaller residues in FS2 are indicated in open circled. FIG. 4C depicts a structure that shows the canonical Bfl-1:BH3 salt bridge between D3f and R88 is observed in the Bfl-1:PUMA complex but not the Bfl-1:FS2 complex. FIG. 4D depicts a structure that shows tryptophan at G1 is rotated into the Bfl-1 binding groove in the Bfl-1:FS2 complex and away from the binding groove in the Bfl-1:PUMA complex. FIG. 4E depicts a structure that shows that in contrast with the solvent exposed arginine at position C3 of the Bfl-1:PUMA complex, R3c is oriented into the BH3 binding groove in the Bfl-1:FS2 complex, forming a hydrogen bond with N51 of Bfl-1.

Figure 5A:
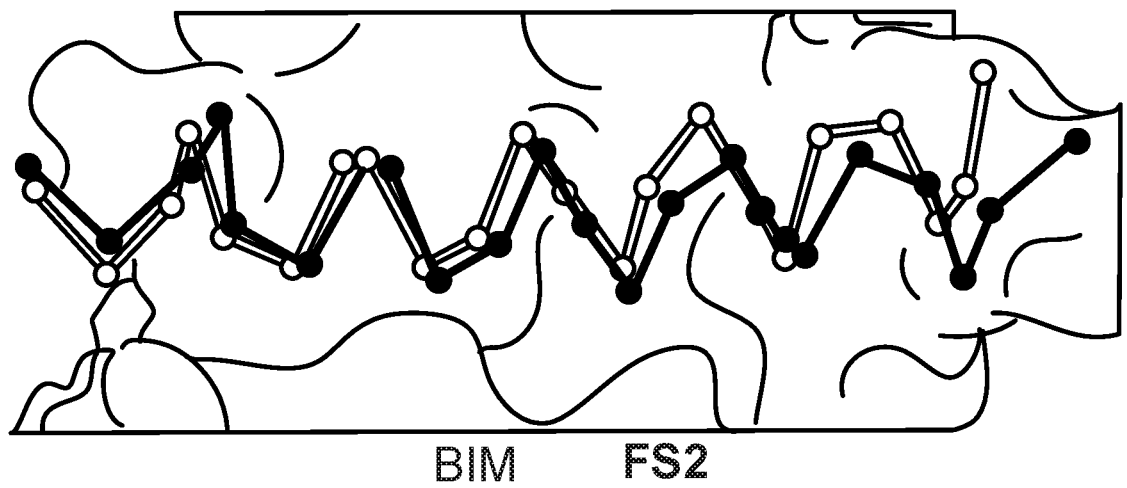
Figure 5B:
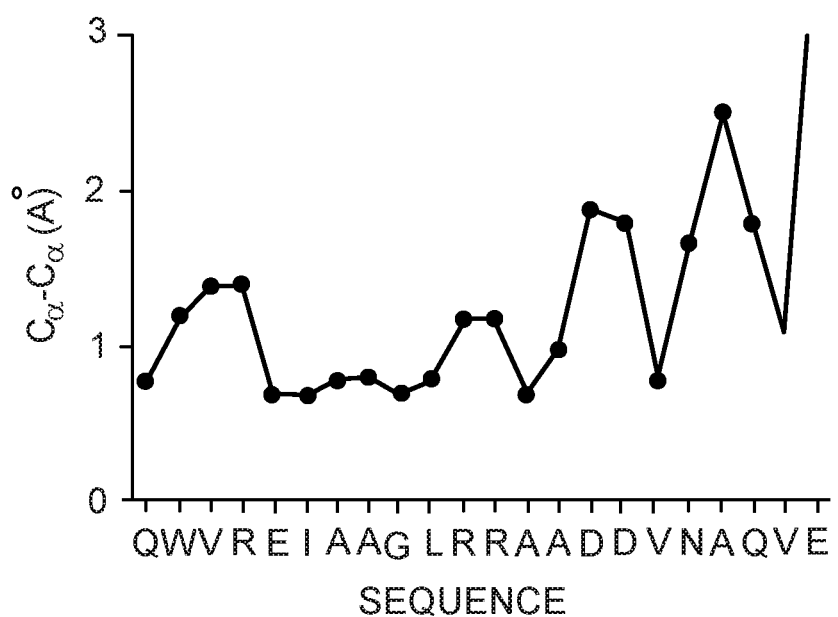

FIG. 5A-E depicts a crystal structure of FS2 bound to human Mcl-1. FIG. 5A shows the binding groove of Mcl-1 (gray, surface) with BIM (light gray, 2PQK[66]) and FS2 (dark gray). FIG. 5B depicts $C_\alpha$-$C_\alpha$ shifts between FS2 and BIM when bound to Mcl-1. FIG. 5C depicts a structure showing that the canonical Bfl-1:BH3 salt bridge between D3f and R92, formed in Mcl-1:BIM, is not observed in the Mcl-1:FS2 complex. FIG. 5D depicts a structure showing that, in contrast with the arginine at position C3 of the Bfl-1:FS2 complex, which makes packing and hydrogen-bond interactions the interface, R3c is oriented away from the BH3 binding groove in the Mcl-1:FS2 complex. FIG. 5E depicts a structure showing that the Mcl-1 binding groove between helix 3 and helix 4 is narrower than the Bfl-1 binding groove, and the N-terminus of FS2 is shifted in the Mcl-1:FS2 structure in comparison with the Bfl-1:FS2 complex.

FIG. 6 is a table of IS values for binding of several BH3 variant peptides to Bfl-1 (target) or Bcl-$x_L$, Mcl-1, Bcl-2, and Bcl-W (undesired competitors).

FIG. 7 is a table quantifying the binding of Puma BH3 variants to Bfl-1 (target) or Bcl-2, Bcl-$x_L$, Bcl-W, and Mcl-1 (undesired competitors).

FIG. 8 is a table quantifying the binding of Puma BH3 variants to Bfl-1 (target) or Bcl-2, Bcl-$x_L$, Bcl-W, and Mcl-1 (undesired competitors).

Figure 9C:
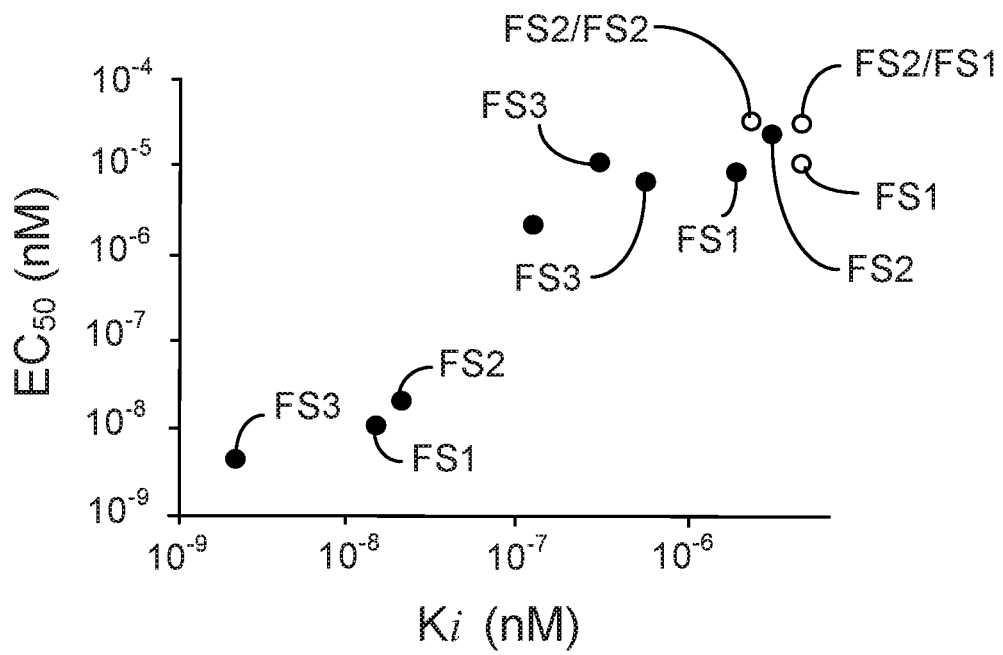
Figure 9D:
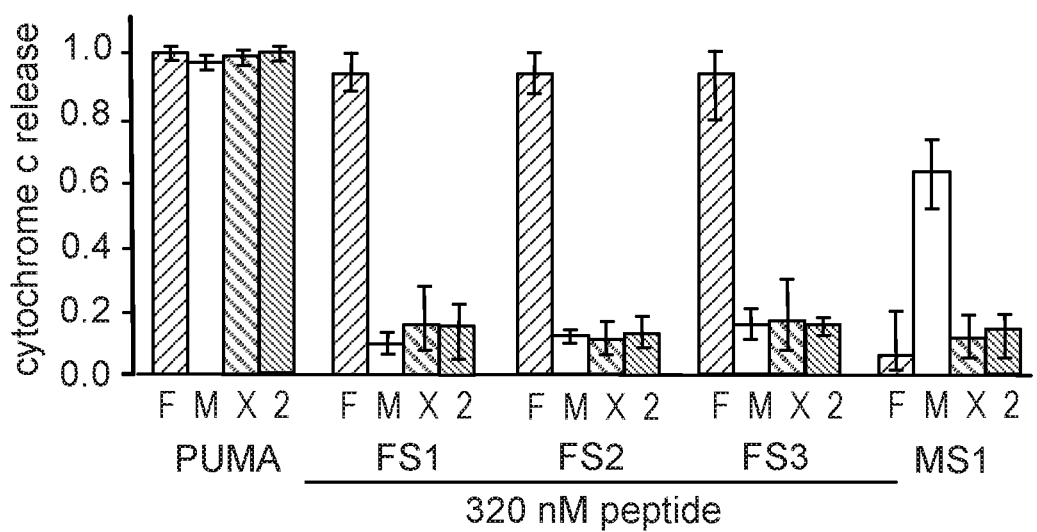

FIG. 9A-D show that designed Bfl-1 inhibitors selectively induce MOMP in Bfl-1 dependent cells. FIG. 9A shows that the BH3 profiling assay detects MOMP by monitoring JC-1 fluorescence in permeabilized cells treated with different peptides. FIG. 9B depicts a bar chart showing depolarization of mitochondria induced by designed peptides in four cell lines that depend on ectopic expression of Mcl-1 (M), Bcl-2 (2), Bcl-$x_L$(X), or Bfl-1(F) for survival. FIG. 9C depicts a chart showing the correlation between $K_i$ in solution studies and $EC_{50}$ values in BH3 profiling. Open circles indicate lower bound estimates of $EC_{50}$ or $K_i$. FIG. 9D depicts a bar chart showing cytochrome c release from the same cell lines in FIG. 9B and FIG. 9C. Data are mean±SD of 3 or more independent measurements.

Figure 10D:
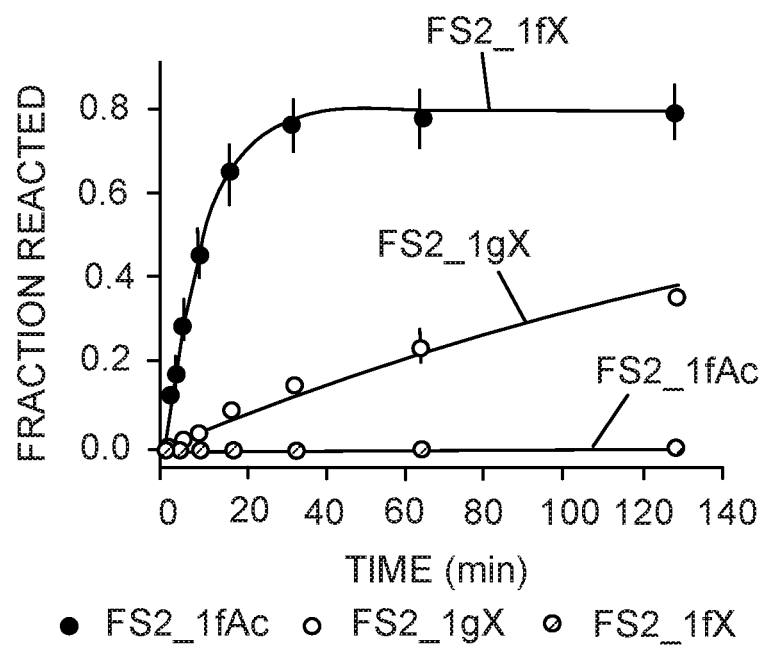
Figure 10E:
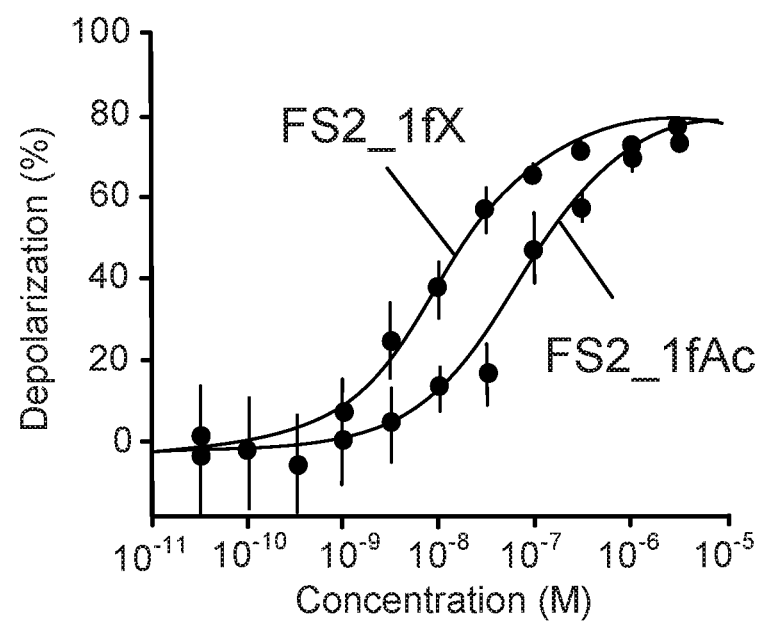
Figure 10F:
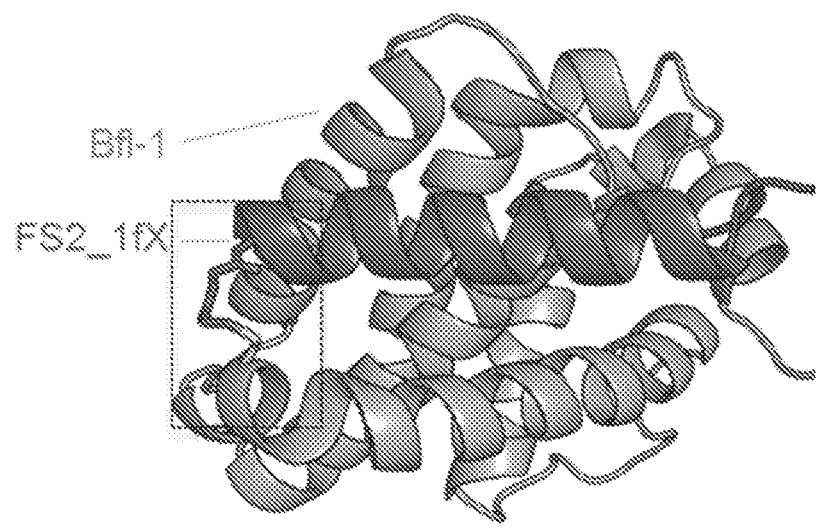
Figure 10G:
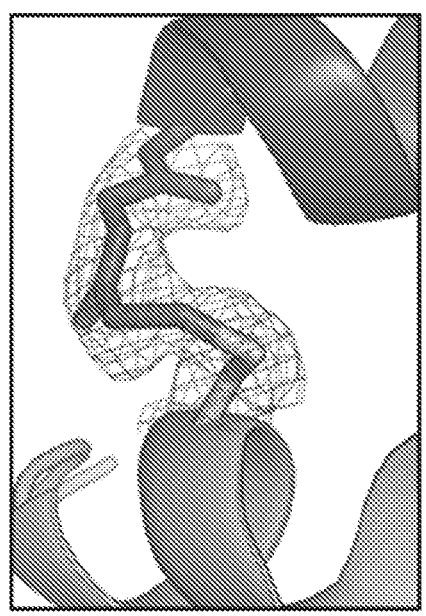

FIG. 10A-G show that an electrophilic variant of FS2 reacts covalently with Bfl-1. FIG. 10A depicts a structure showing that C55 in Bfl-1 is close to the BH3 binding groove in BIM:Bfl-1 structure 2VM6[29]. FIG. 10B and FIG. 10C depict modeling suggesting two ways in which an N-terminal acrylamide group could be incorporated into a BH3 peptide with good reaction geometry, leading to peptides FS2_1gX (modification shown in FIG. 10B) or FS2_1fX (modification shown in FIG. 10C). FIG. 10D depicts a chart showing that FS2_1fX reacted more rapidly with Bfl-1 than FS2_1gX. Bfl-1 crosslinking as a function of reaction time was measured using gel-shift assays; data are mean±SD of 2 or more independent measurements. Crosslinking did not occur with the acetylated control peptide FS2_1fAc. FIG. 10E depicts a graph showing that FS2_1fX was more potent than FS2_1fAc in BH3 profiling assays of Bfl-1 dependent cells. Data are mean±SD of 3 or more independent measurements. FIG. 10F depicts an X-ray structure of Bfl-1 covalently cross-linked to FS2_1fX. FIG. 10G shows an electron density map of covalent crosslink between FS2_1fX and Bfl-1.

FIG. 11 is a table of sequences of several Bfl-1-targeting BH3 peptides that have been modified with electrophiles as shown.

Figure 12A:
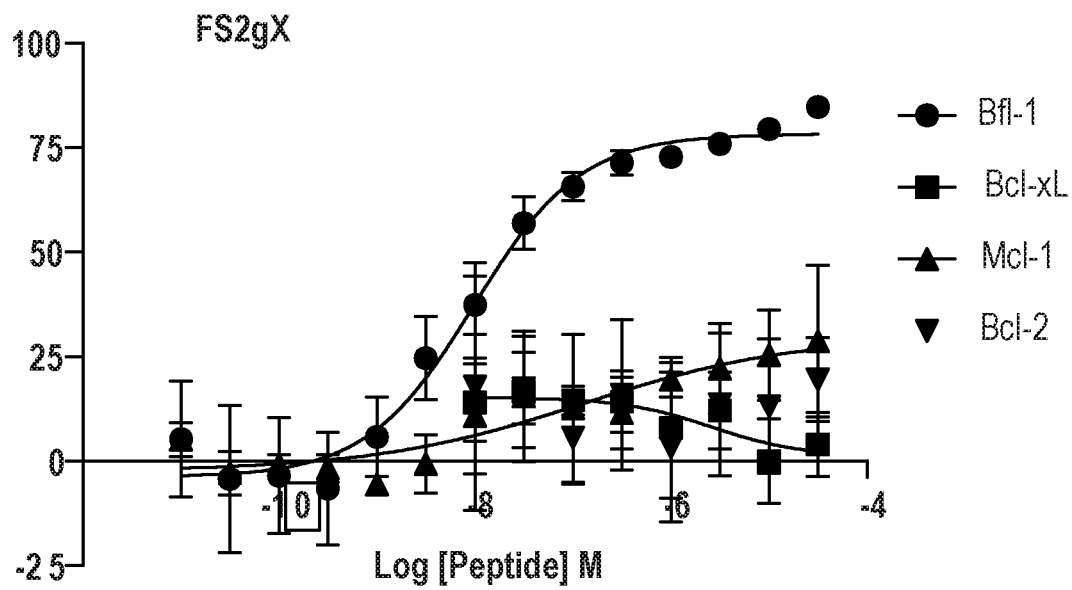
Figure 12B:
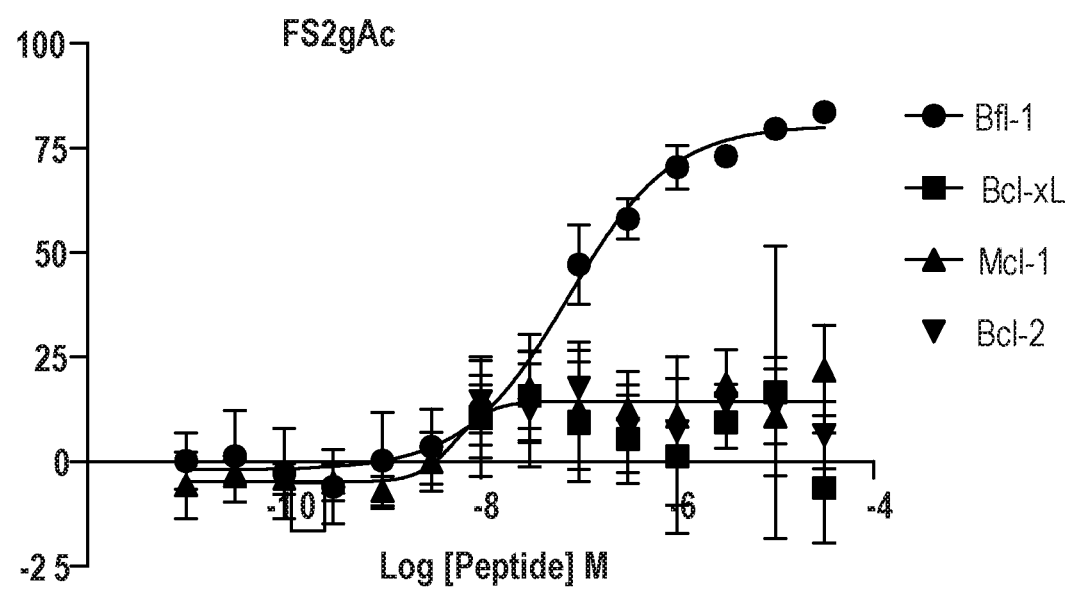

FIG. 12A-B are graphs of the BH3 profiling of FS2gX (FIG. 12A) and FS2gAc (FIG. 12B). Error bars indicate the standard deviation over 3 or more replicates.

DETAILED DESCRIPTION

The present disclosure provides compounds for the targeting of protein Bfl-1. The compounds described herein comprise a polypeptide that binds relatively tightly and selectively to Bfl-1 and can inhibit its function. The compounds include covalent and non-covalent inhibitors of Bfl-1.

Compounds

As described herein, the compounds comprise a polypeptide. Amino acids are the building blocks of the peptides herein. The term "amino acid" refers to a molecule containing both an amino group, a carboxyl group, and a side chain. Amino acids suitable for inclusion in the peptides disclosed herein include, without limitation, natural alpha-amino acids such as D- and L-isomers of the 20 common naturally occurring alpha-amino acids found in peptides (e.g., Ala (A), Arg (R), Asn (N), Cys (C), Asp (D), Gln (Q), Glu (E), Gly (G), His (H), Ile (I), leu (L), Lys (K), Met (M), Phe (F), Pro (P), Ser (S), Thr (T), Trp (W), Tyr (Y), and Val (V), unnatural alpha-amino acids (including, but not limited to α,α-disubstituted and N-alkylated amino acids), natural beta-amino acids (e.g., beta-alanine), and unnnatural beta-amino acids. Amino acids used in the construction of peptides of the present invention can be prepared by organic synthesis, or obtained by other routes, such as, for example, degradation of or isolation from a natural source.

There are many known unnatural amino acids any of which may be included in the peptides of the present invention. Some examples of unnatural amino acids are 4-hydroxypro line, desmosine, gamma-aminobutyric acid, beta-cyanoalanine, norvaline, norleucine, homoleucine, ornithine, homoglutamate, azidoalanine, cyclohexylalanine, cyclohexanecarboxylic acid, d-phenylglycine, d-histidine, d-leucine, d-cyclohexylalanine, 4,4-biphenylalanine, 2-aminoheptanoic acid, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and/para-substituted phenylalanines (e.g., substituted with —C(=O)C6H5; —CF3; —CN; -halo; —NO2; CH3), disubstituted phenylalanines, substituted tyrosines (e.g., further substituted with -Q=O)C6H5; —CF3; —CN; -halo; —NO2; CH3), and statine. Additionally, amino acids can be derivatized to include amino acid residues that are hydroxylated, phosphorylated, sulfonated, acylated, and glycosylated, to name a few.

In some instances, peptides include only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide or polypeptide may be modified, for example, by the addition of a chemical entity such as a carbohydrate group, an electrophilic group, a hydroxyl group, a phosphate group, a farnesyl group, an isofarnesyl group, a fatty acid group, a linker for conjugation, functionalization, or other modification, etc. In some cases, one or more of the amino acids in a peptide or polypeptide may be modified by the addition of a peptide, e.g., a peptide tag. In some instances, the peptide is a cell penetrating peptide tag that increases the penetration of a cell by the peptide or polypeptide. Cell penetrating peptide tags are known in the art, and can include, for example, trans-activating transcriptional activator (TAT) peptide (GRKKRRQRRRPPQ), a pVEC (cadherin residues 615-632) peptide (LLIILRRRIRKQAHAHSK), Pep-1 peptide (KETWWETWWTEWSQPKKKRKV), penetratin (Antennapedia residues 43-58) peptide (RQIKIWFQNRRMKWKK), polyarginine (6 amino acids<n<12 amino acids), fibroblast growth factor 4 (FGF4)-derived peptide, transportan (Galanine/Mastoparan) peptide (GWTLNSAGYLLGKINLKALAALAKKIL), MPG peptide (GALFLGFLGAAGSTMGAWSQPKKKRKV), MAP peptide (KLALKLALKALKAALKLA), RGW3 peptide (RRWWRRWRR), CPP9 peptide (CYGGRGDTP), or CPP12 peptide (see Bechara et al., *FEBS Lett.,* 587(12): 1693-1702, 2013; Qian et al., *Biochem.,* 55(18):2601-2612, 2016). In some instances, the peptide is an affinity tag that contains an epitope. Affinity tags are known in the art, and can include, for example, an AviTag, a Flag-tag, an HA-tag, a His-tag, a Myc-tag, an S-tag, a V5-tag, and a VSV-tag. One or more peptide tag, e.g., a cell penetrating peptide tag or an affinity tag, can be attached to the N-terminus of the polypeptide or to the C-terminus of the polypeptide. In some cases, one or more peptide tag, e.g., a cell penetrating peptide tag and/or an affinity tag, can be attached to the N-terminus of the polypeptide and to the C-terminus of the polypeptide.

A compound comprising a peptide described herein can include a peptide that is modified, for example, by the addition of a chemical entity such as a carbohydrate group, an electrophilic group, a hydroxyl group, a phosphate group, a farnesyl group, an isofarnesyl group, a fatty acid group, a linker for conjugation, functionalization, or other modification, etc. In some cases, the compound comprises a peptide and an electrophilic group that is attached to the N-terminus of the peptide via an amide bond. For example, the compound can comprise a polypeptide with an acrylamide attached to the N-terminus of the peptide via an amide bond. In some cases, an electrophilic group is attached to the N-terminus of a peptide described herein and the N-terminal amino acid of the peptide is a G or a V. In some cases, an electrophilic group is attached to the N-terminus of a peptide described herein and the N-terminal amino acid of the peptide is a G. In some cases, the compound comprises a peptide and an electrophilic group that is attached to an amino acid of the peptide via the amino group of the side chain of the amino acid. For example, the compound can comprise a peptide and an electrophilic group, where the electrophilic group is attached to the amino group of the side chain of DAP, DAB, ornithine and/or lysine. (See, for example, Stebbins JL., et al. "Structure-based design of covalent Siah inhibitors." Chem Biol. 2013 Aug. 22; 20(8): 973-82. Epub 2013 Jul. 25, which is incorporated herein in its entirety).

A non-limiting list of electrophilic groups that can be included in the compounds described herein includes: α,β-unsaturated carbonyl derivatives including acrylamide, cyanoacrylamides, and other electron withdrawing groups; vinyl sulfones; acrylonitrile; epoxides; electrophilic ketones including acyloxymethyl ketone (AOMK) and chloromethyl ketone (CMK); chloracetamides (CA); iodoacetamides (IA); and semicarbazide. In some embodiments the electrophilic group is attached to a peptide described herein. Additional examples of electrophilic groups are known in the art, see, for example, Shannon and Weerapana, 2015 (Shannon, D. A. & Weerapana, E. Covalent protein modification: the current landscape of residue-specific electrophiles. *Curr. Opin. Chem. Biol.* 24, 18-26 (2015); which is incorporated herein in its entirety).

In some instances, the compound can include (e.g., comprise, consist essentially of, or consist of) a peptide of at least sixteen (e.g., 16, 17, 18, 19, 20, 21, 22, 23, 24, 25, 26, 27, etc.) contiguous amino acids of any of SEQ ID NOs: 1-15. In some cases, the peptides include a sequence no longer than u 40, 35, 30, 25, 24, 23, 22, 21, 20, 19, 18, 17, 16, 15 or 14 amino acids. In some cases, the peptides include a sequence of about 24 amino acids. In some cases, the peptides include a sequence of about 23 amino acids. In some cases, the peptide is or is no longer than 22 amino acids. In some cases, the peptide is or is no longer than 21 amino acids. In some cases, the peptides include modifications and/or additions on at least one terminus. For example, the peptide can include the amino acid sequence of any of SEQ ID NOs: 1-15 with additions on the C-terminus, on the N-terminus, or on both the C- and the N-terminus. In some instances, the compound includes a peptide and an electrophilic group that is attached to the N-terminus of the peptide and the peptide includes a modification and/or additions on the C-terminus. In some cases, the at least sixteen contiguous amino acids of any of SEQ ID NOs: 1-15 are part of a longer polypeptide. In some cases, the peptide includes at least 21 contiguous amino acids of any of SEQ ID NOs: 1-15 and the peptide is part of a longer peptide.

The compounds described herein can include a peptide comprising an amino acid sequence selected from SEQ ID NOs: 1-15. In some cases, at least two amino acids in the sequence are replaced by another amino acid (e.g., 2, 3, 4, 5, 6, or 7). In some cases, no more than 2 amino acids are replaced by another amino acid (e.g., 0, 1, or 2). In some compounds, none of the amino acids are replaced by another amino acid. In some cases, the compound comprises a peptide that comprises the amino acid sequence of SEQ ID NO: 1. In some embodiments A2 is A, E, I, K, L, P, Q, T, V, or a conservative substitution thereof. In some embodiments, E2 is G, A, C, D, S, Y, or a conservative substitution thereof. In some embodiments, G2 is Q, C, D, F, G, H, I, L, N, R, S, V, Y, or a conservative substitution thereof. In some embodiments, D3 is M, A, C, F, G, I, L, P, R, S, T, V, or a conservative substitution thereof. In some embodiments, G3 is D, E, G, I, K, L, M, N, Q, V, or a conservative substitution thereof. In some embodiments, A4 is L, A, D, F, G, I, N, P, S, T, V, Y, or a conservative substitution thereof. In some embodiments, E4 is Y, A, F, I, L, P, S, T, V, or a conservative substitution thereof. See, for example, point mutations in FIG. 1B. In some cases, G1 is 4,4-biphenylalanine or azidoalanine. In some cases, C2 is 2,3-diaminopropanoic acid. In some cases, D2 is 2,4-diaminobutyric acid, norleucine, homoleucine, cyclohexylalanine, or 2-aminoheptanoic acid. In some cases, A3 is cyclohexylalanine or homoleucine. In some cases, D3 is d-phenylglycine, d-histidine, d-leucine, α-aminoisobutyric acid, or cyclohexanecarboxylic acid. In some cases, E3 is ornithine, 2,4-diaminobutyric acid or 2,3-diaminopropionic acid. In some cases, F3 is homoglutamate. In some cases, 4A is d-cyclohexylalanine.

In some instances, a "conservative amino acid substitution" can include substitutions in which one amino acid residue is replaced with another amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The compounds described herein can include at least two modified amino acids that together form an internal (intramolecular) cross-link (or staple), wherein the at least two modified amino acids are separated by: (A) three amino acid (i.e., i, i+4) or (B) six amino acids (i.e., i, i+7). In the case of a cross-link between i and i+4 the cross-link can be a C8 alkene (e.g., with a single double bond between the 4th and 5th carbons) alkylene or alkenylene. In the case of a cross-link between i and i+7 the cross-link can be a C11, C12 or C13 alkylene or alkenylene. When the cross-link is an alkenylene there can one or more double bonds. In the case of a cross-link between i and i+4 the cross-link can be a C8 alkyl or alkene. In the case of a cross-link between i and i+7 the cross-link can be a C11, C12 or C13 alkyl or alkene (e.g., a C11 alkene having a single double bond). When the cross-link is an alkene there can be one or more double bonds.

A cross-link can stabilize the alpha-helical secondary structure of a peptide that is predisposed to have a native alpha-helical conformation. The constrained secondary structure may, for example, increase the peptide's resistance to proteolytic cleavage, may increase the peptide's thermal stability, may increase the peptide's hydrophobicity, may allow for better penetration of the peptide into the target cell's membrane (e.g., through an energy-dependent transport mechanism such as pinocytosis), and/or may lead to an improvement in the peptide's biological activity relative to the corresponding uncross-linked (e.g., "unstitched" or "unstapled") peptide. Various embodiments of staples, stapled peptides, and the methods of creating stapled peptides are known in the art, for example WO 2008121767 and WO 2010/068684, which are both hereby incorporated by reference.

Peptides can contain one or more asymmetric centers and thus occur as racemates and racemic mixtures, single enantiomers, individual diastereomers and diastereomeric mixtures and geometric isomers (e.g. Z or cis and E or trans) of any olefins present. For example, peptides disclosed herein can exist in particular geometric or stereoisomeric forms, including, for example, cis- and trans-isomers, R- and S-enantiomers, diastereomers, (D)-isomers, (L)-isomers, the racemic mixtures thereof, and other mixtures thereof. Enantiomers can be free (e.g., substantially free) of their corresponding enantiomer, and/or may also be optically enriched. "Optically enriched," as used herein, means that the compound is made up of a significantly greater proportion of one enantiomer. In certain embodiments substantially free means that a composition contains at least about 90% by weight of a preferred enantiomer. In other embodiments the compound is made up of at least about 95%, 98%, or 99% by weight of a preferred enantiomer. Preferred enantiomers may be isolated from racemic mixtures using techniques known in the art, including, but not limited to, for example, chiral high pressure liquid chromatography (HPLC) and the formation and crystallization of chiral salts or prepared by asymmetric syntheses (see, e.g., Jacques, et al, Enantiomers, Racemates and Resolutions (Wiley Interscience, New York, 1981); Wilen, S. H., et al., Tetrahedron 33:2725 (1977); Eliel, EX. Stereochemistry of Carbon Compounds (McGraw-Hill, N Y, 1962); Wilen, S. H. Tables of Resolving Agents and Optical Resolutions p. 268 (EX. Eliel, Ed., Univ. of Notre Dame Press, Notre Dame, Ind. 1972). All such isomeric forms of these compounds are expressly included in the present invention.

Peptides can also be represented in multiple tautomeric forms, in such instances, the invention expressly includes all tautomeric forms of the compounds described herein (e.g., isomers in equilibrium (e.g., keto-enol), wherein alkylation at multiple sites can yield regioisomers), regioisomers, and oxidation products of the compounds disclosed herein (the invention expressly includes all such reaction products). All such isomeric forms of such compounds are included as are all crystal forms.

In some instances, alpha disubstituted amino acids are used in the polypeptide to improve the stability of the alpha helical secondary structure. However, alpha disubstituted amino acids are not required, and instances using mono-alpha substituents (e.g., in the tethered amino acids) are also envisioned.

The addition of polyethelene glycol (PEG) molecules can improve the pharmacokinetic and pharmacodynamic properties of the polypeptide. For example, PEGylation can reduce renal clearance and can result in a more stable plasma concentration. PEG is a water soluble polymer and can be represented as linked to the polypeptide as formula: XO—$(CH_2CH_2O)_n$—$CH_2CH_2$—Y where n is 2 to 10,000 and X is H or a terminal modification, e.g., a C1-4 alkyl; and Y is an amide, carbamate or urea linkage to an amine group (including but not limited to, the epsilon amine of lysine or the N-terminus) of the polypeptide. Y may also be a maleimide linkage to a thiol group (including but not limited to, the thiol group of cysteine). Other methods for linking PEG to a polypeptide, directly or indirectly, are known to those of ordinary skill in the art. The PEG can be linear or branched. Various forms of PEG including various functionalized derivatives are commercially available. PEG having degradable linkages in the backbone can be used. For example, PEG can be prepared with ester linkages that are subject to hydrolysis. Conjugates having degradable PEG linkages are described in WO 99/34833; WO 99/14259, and U.S. Pat. No. 6,348,558.

In certain embodiments, a macromolecular polymer (e.g., PEG) is attached to a compound described herein through an intermediate linker. In certain embodiments, the linker is made up of from 1 to 20 amino acids linked by peptide bonds, wherein the amino acids are selected from the 20 naturally occurring amino acids. Some of these amino acids may be glycosylated, as is well understood by those in the art. In other embodiments, the 1 to 20 amino acids are selected from glycine, alanine, proline, asparagine, glutamine, and lysine. In other embodiments, a linker is made up of a majority of amino acids that are sterically unhindered, such as glycine and alanine. Non-peptide linkers are also possible. For example, alkyl linkers such as —$NH(CH_2)_nC(O)$—, wherein n=2-20 can be used. These alkyl linkers may further be substituted by any non-sterically hindering group such as lower alkyl (e.g., C1-C6) lower acyl, halogen (e.g., Cl, Br), CN, $NH_2$, phenyl, etc. U.S. Pat. No. 5,446,090 describes a bifunctional PEG linker and its use in forming conjugates having a peptide at each of the PEG linker termini.

The peptides can also be modified, e.g., to further facilitate cellular uptake or increase in vivo stability, in some embodiments. For example, acylating or PEGylating a peptidomimetic macrocycle facilitates cellular uptake, increases bioavailability, increases blood circulation, alters pharmacokinetics, decreases immunogenicity and/or decreases the needed frequency of administration. In another example, the peptides may be modified by the addition of a cell penetrating peptide tag that facilitates the penetration of a cell, such as, e.g., a TAT peptide, a pVEC peptide, a Pep-1 peptide, a penetratin peptide, a polyarginine peptide, an FGF4-derived peptide, a transportan peptide, an MPG peptide, a MAP peptide, an RGW3 peptide, a CPP9 peptide, or a CPP12 peptide. Therefore, the compounds comprising a peptide disclosed herein can comprise a peptide that has been modified, e.g., to further facilitate cellular uptake, increase in vivo stability, or have an enhanced ability to penetrate cell membranes, in some embodiments.

Peptide bonds can be replaced, e.g., to increase physiological stability of the peptide, by: a retro-inverso bonds (C(O)—NH); a reduced amide bond (NH—$CH_2$); a thiomethylene bond (S—$CH_2$ or $CH_2$—S); an oxomethylene bond (O—$CH_2$ or $CH_2$—O); an ethylene bond ($CH_2$—$CH_2$); a thioamide bond (C(S)—NH); a trans-olefin bond (CH=CH); a fluoro substituted trans-olefin bond (CF=CH); a ketomethylene bond (C(O)—CHR) or CHR—C(O) wherein R is H or $CH_3$; and a fluoro-ketomethylene bond (C(O)—CFR or CFR—C(O) wherein R is H or F or $CH_3$.

Using these methods, the polypeptides can be further modified by: acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. As indicated above, peptides can be conjugated to, for example, polyethylene glycol (PEG); alkyl groups (e.g., C1-C20 straight or branched alkyl groups); fatty acid radicals; and combinations thereof. As described herein, the peptides can be further modified to include an electrophilic group.

Therefore, a compound comprising a polypeptide described herein can include a polypeptide that is modified by: acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. As indicated above, a compound comprising a polypeptide can include peptides that can be conjugated to, for example, polyethylene glycol (PEG); alkyl groups (e.g., C1-C20 straight or branched alkyl groups); fatty acid radicals; and combinations thereof.

In some instances, the peptides described herein can include a detectable label. As used herein, a "label" refers to a moiety that has at least one element, isotope, or functional group incorporated into the moiety which enables detection of the peptide to which the label is attached. Labels can be directly attached (ie, via a bond) or can be attached by a linker (e.g., such as, for example, a cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene, or any combination thereof, which can make up a linker). Labels can be attached to a peptide at any position that does not interfere with the biological activity or characteristic of the inventive polypeptide that is being detected.

Labels can include: labels that contain isotopic moieties, which may be radioactive or heavy isotopes, including, but not limited to, $^{2}H$, $^{3}H$, $^{13}C$, $^{14}C$, $^{15}N$, $^{31}P$, $^{32}P$, $^{35}S$, $^{67}Ga$, $^{99m}TC$ (Tc-99m), $^{111}In$, $^{123}I$, $^{125}I$, $^{169}Yb$, and $^{186}Re$, labels that include immune or immunoreactive moieties, which may be antibodies or antigens, which may be bound to enzymes (e.g., such as horseradish peroxidase); labels that are colored, luminescent, phosphorescent, or include fluorescent moieties (e.g., such as the fluorescent label FITC); labels that have one or more photoaffinity moieties; labels that have ligand moieties with one or more known binding partners (such as biotin-streptavidin, FK506-FKBP, etc.).

In some instances, labels can include one or more photoaffinity moieties for the direct elucidation of intermolecular interactions in biological systems. A variety of known photophores can be employed, most relying on photoconversion of diazo compounds, azides, or diazirines to nitrenes or carbenes (see, e.g., Bayley, H., Photogenerated Reagents in Biochemistry and Molecular Biology (1983), Elsevier, Amsterdam, the entire contents of which are incorporated herein by reference). In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

Labels can also be or can serve as imaging agents. Exemplary imaging agents include, but are not limited to, those used in positron emissions tomography (PET), computer assisted tomography (CAT), single photon emission computerized tomography, x-ray, fluoroscopy, and magnetic resonance imaging (MRI); anti-emetics; and contrast agents. Exemplary diagnostic agents include but are not limited to, fluorescent moieties, luminescent moieties, magnetic moieties; gadolinium chelates (e.g., gadolinium chelates with DTPA, DTPA-BMA, DOTA and HP-DO3A), iron chelates, magnesium chelates, manganese chelates, copper chelates, chromium chelates, iodine-based materials useful for CAT and x-ray imaging, and radionuclides. Suitable radionuclides include, but are not limited to, $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y $^{97}$Ru, $^{100}$Pd, $^{101}$mRh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{75}$Br $^{77}$Br, $^{99}$mTC, $^{14}$C, $^{13}$N, $^{15}$O, $^{32}$P, $^{33}$P, and $^{18}$F.

Fluorescent and luminescent moieties include, but are not limited to, a variety of different organic or inorganic small molecules commonly referred to as "dyes," "labels," or "indicators." Examples include, but are not limited to, fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art (see, e.g., U.S. Patent Publication 2004/0067503; Valeur, B., "Molecular Fluorescence: Principles and Applications," John Wiley and Sons, 2002; and Handbook of Fluorescent Probes and Research Products, Molecular Probes, 9th edition, 2002).

Methods of synthesizing the compounds described herein are known in the art. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3d. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

For example, the peptides of this invention can be made by chemical synthesis methods, which are well known to the ordinarily skilled artisan. See, for example, Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the α-NH2 protected by either t-Boc or Fmoc chemistry using side chain protected amino acids on, for example, an Applied Biosystems Peptide Synthesizer Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides could be made by conjoining individual synthetic peptides using native chemical ligation. Alternatively, the longer synthetic peptides can be synthesized by well-known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

Additionally or alternatively, the peptides can be made in a high-throughput, combinatorial fashion, e.g., using a high-throughput multiple channel combinatorial synthesizer available from Advanced Chemtech.

Again, methods suitable for obtaining (e.g., synthesizing), stapling, and purifying the peptides disclosed herein are also known in the art (see, e.g., Bird et. al., Methods in Enzymol., 446:369-386 (2008); Bird et al, Current Protocols in Chemical Biology, 2011; Walensky et al., Science, 305:1466-1470 (2004); Schafmeister et al., J. Am. Chem. Soc., 122:5891-5892 (2000); U.S. patent application Ser. No. 12/525,123, filed Mar. 18, 2010; and U.S. Pat. No. 7,723,468, issued May 25, 2010, each of which are hereby incorporated by reference in their entirety).

In some embodiments, the peptides are substantially free of contaminants or are isolated. Methods for purifying peptides include, for example, synthesizing the peptide on a solid-phase support. Following cyclization, the solid-phase support may be isolated and suspended in a solution of a solvent such as DMSO, DMSO/dichloromethane mixture, or DMSO/NMP mixture. The DMSO/dichloromethane or DMSO/NMP mixture may comprise about 30%, 40%, 50% or 60% DMSO. In a specific embodiment, a 50%/50% DMSO/NMP solution is used. The solution may be incubated for a period of 1, 6, 12 or 24 hours, following which the resin may be washed, for example with dichloromethane or NMP. In one embodiment, the resin is washed with NMP. Shaking and bubbling an inert gas into the solution may be performed.

Pharmaceutical Compositions

One or more of the compounds (e.g., compound comprising peptides) disclosed herein (e.g., one or more of SEQ ID NOs: 1-15) can be formulated for use as or in pharmaceutical compositions. Such compositions can be formulated or adapted for administration to a subject via any route, e.g., any route approved by the Food and Drug Administration (FDA). Exemplary methods are described in the FDA's CDER Data Standards Manual, version number 004 (which is available at fda.give/cder/dsm/DRG/drg00301.htm). For example, compositions can be formulated or adapted for administration by inhalation (e.g., oral and/or nasal inhalation (e.g., via nebulizer or spray)), injection (e.g., intravenously, intra-arterial, subdermally, intraperitoneally, intramuscularly, and/or subcutaneously); and/or for oral administration, transmucosal administration, and/or topical administration (including topical (e.g., nasal) sprays and/or solutions).

In some instances, pharmaceutical compositions can include an effective amount of one or more peptides. The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., treatment of cancer).

The therapeutic and/or biologic agents can be administered in an effective amount, at dosages and for periods of time necessary to achieve the desired result. An effective amount can be administered in one or more administrations, applications or dosages. A therapeutically effective amount of a pharmaceutical composition (i.e., an effective dosage) depends on the pharmaceutical composition selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the pharmaceutical compositions described herein can include a single treatment or a series of treatments.

Dosage regimens can be adjusted to provide the optimum therapeutic response. For example, several divided doses can be administered daily or the dose can be proportionally reduced as indicated by the exigencies of the therapeutic situation.

A pharmaceutical composition provided herein can include one or more peptides and any pharmaceutically acceptable carrier, delivery agent, and/or vehicle. In some instances, pharmaceuticals can further include one or more additional therapeutic agents in amounts effective for achieving a modulation of disease or disease symptoms.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound. As used herein the term "pharmaceutically acceptable carrier" includes solvents, dispersion media, coatings, antibacterial and antifungal agents, isotonic and absorption delaying agents, and the like, compatible with pharmaceutical administration.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

The pharmaceutical compositions of this invention may contain any conventional non-toxic pharmaceutically-acceptable carriers, adjuvants or vehicles. Carrier proteins can include any protein that increases or enhances immunogenicity in a subject. Exemplary carrier proteins are described in the art (see, e.g., Fattom et al., Infect. Immun., 58:2309-2312, 1990; Devi et al., Proc. Natl. Acad. Sci. USA 88:7175-7179, 1991; Li et al., Infect. Immun. 57:3823-3827, 1989; Szu et al., Infect. Immun. 59:4555-4561,1991; Szu et al., J. Exp. Med. 166:1510-1524, 1987; and Szu et al., Infect. Immun. 62:4440-4444, 1994). Polymeric carriers can be a natural or a synthetic material containing one or more primary and/or secondary amino groups, azido groups, or carboxyl groups. Carriers can be water soluble.

In some instances, one or more peptides disclosed herein can be conjugated, for example, to a carrier protein. Such conjugated compositions can be monovalent or multivalent. For example, conjugated compositions can include one peptide disclosed herein conjugated to a carrier protein. Alternatively, conjugated compositions can include two or more peptides disclosed herein conjugated to a carrier.

As used herein, when two entities are "conjugated" to one another they are linked by a direct or indirect covalent or non-covalent interaction. In certain embodiments, the association is covalent. In other embodiments, the association is non-covalent. Non-covalent interactions include hydrogen bonding, van der Waals interactions, hydrophobic interactions, magnetic interactions, electrostatic interactions, etc. An indirect covalent interaction is when two entities are covalently connected, optionally through a linker group.

In some cases, the pH of the formulation may be adjusted with pharmaceutically acceptable acids, bases or buffers to enhance the stability of the formulated compound or its delivery form. The term parenteral as used herein includes subcutaneous, intra-cutaneous, intra-venous, intra-muscular, intra-articular, intra-arterial, intra-synovial, intra-sternal, intra-thecal, intra-lesional and intra-cranial injection or infusion techniques.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, N.Y.). As previously mentioned, pharmaceutical compositions can be in the form of a solution or powder for inhalation and/or nasal administration. Such compositions may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

Pharmaceutical compositions can be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

Alternatively or in addition, pharmaceutical compositions can be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Methods of Treatment

The disclosure includes methods of using the compounds (e.g., compounds comprising the peptides) described herein for the prophylaxis and/or treatment of cancer. The terms "treat" or "treating," as used herein, refers to partially or completely alleviating, inhibiting, ameliorating, and/or relieving the disease or condition from which the subject is suffering. Often, treating with the compounds described herein results in apoptosis of the cancer cells; thus the treatment can result in a reduction in tumor or cancer cells and a return to or increase in normal cells.

In some embodiments, the present disclosure provides methods for using any one or more of the peptides or pharmaceutical compositions (indicated below as 'X') disclosed herein in the following methods: Substance X for use as a medicament in the treatment of one or more diseases or conditions disclosed herein (e.g., cancer, referred to in the following examples as 'Y'). Use of substance X for the manufacture of a medicament for the treatment of Y; and substance X for use in the treatment of Y.

In general, methods include administering a therapeutically effective amount of one or more of the peptides herein, to a subject who is in need of, or who has been determined to be in need of, such treatment, e.g., in or as a pharmaceutical composition, and optionally repeating administration as required for the prophylaxis or treatment of a cancer.

Skilled practitioners will appreciate that a subject who is in need of, such treatment, can be diagnosed by a physician (or veterinarian, as appropriate for the subject being diagnosed) as suffering from or at risk for a condition described herein, e.g., cancer, by any method known in the art, e.g., by assessing a patient's medical history, performing diagnostic tests, and/or by employing imaging techniques.

The peptides described herein can also be used to predict how responsive or sensitive to chemotherapy a subject's tumor or cancer is likely to be.

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Treatment of carcinomas, adenocarcinomas, and sarcomas is within the present disclosure. The term "carcinoma" is art recognized and refers to malignancies of epithelial or endocrine tissues. The term also includes carcinosarcomas, which include malignant tumors composed of carcinomatous and sarcomatous tissues. "Adenocarcinoma" refers to a carcinoma derived from glandular tissue or in which the tumor cells form recognizable glandular structures. The term "sarcoma" is art recognized and refers to malignant tumors of mesenchymal derivation.

Cancers that may be treated using the methods, compositions, and devices of the present invention include, for example, cancers, e.g., tumors, of the stomach, colon, rectum, mouth/pharynx, esophagus, larynx, liver, pancreas, lung, breast, cervix uteri, corpus uteri, ovary, prostate, testis, bladder, skin, bone, kidney, brain/central nervous system, head, neck and throat; sarcomas, choriocarcinomas, and lymphomas, among others. Metastatic tumors can be treated using methods described herein. For example, performing a treatment method described herein on a tumor located at one site in the subject's body (e.g., a primary tumor), can stimulate the subject's immune defenses against the tumor and cause an immune attack on tumors of the same or even different type of at another site(s) in the subject's body (e.g., a metastatic tumor). A metastatic tumor can arise from a multitude of primary tumor types, including but not limited to those of prostate, colon, lung, breast, bone, and liver origin. Metastases develop, e.g., when tumor cells shed from a primary tumor adhere to vascular endothelium, penetrate into surrounding tissues, and grow to form independent tumors at sites separate from a primary tumor.

Cancers that may be treated using the methods, compositions, and devices of the present invention also include blood cancers, for example, cancers of the bone marrow, blood, and lymphatic system (which includes, e.g., the lymph nodes and lymphatic vessels). Blood cancers include, for example, leukemia, myelomas, and lymphomas.

Methods of Detecting Cancer Cells

The disclosure includes methods of using compounds described herein for detecting the presence of Bfl-1 in cells, e.g., cancer or tumor cells. A cell can be contacted with one or more compounds described herein, such as one or more peptides that include a detectable label, to detect the presence of Bfl-1. For example, a cell can be contacted with a peptide attached to detectable label described herein that is used as a probe that binds to Bfl-1. Binding of the peptide to the Bfl-1 in the cell can then be detected by using any of the methods known in the art for detecting and quantifying binding of labeled peptides to proteins, for example, histology, FACS, or western blot.

The disclosure includes methods of using the compounds described herein for detecting cancer or tumor cells that are characterized by expressing Bfl-1, for example, cells that are Bfl-1 dependent, have Bfl-1-induced resistance to chemotherapeutics, or overexpress Bfl-1. The assay to diagnose these cancer cells involves contacting cells with the compounds described herein, and measuring the mitochondrial outer membrane permeabilization (MOMP) of the cell. In some cases, the assay includes, permeablizing the cancer cell, contacting cells with the compounds described herein, and measuring the mitochondrial outer membrane permeabilization (MOMP) of the cell. In some cases, the assay includes, isolating mitochondria from the cells of interest, contacting the cells with the compounds described herein, and measuring the mitochondrial outer membrane permeabilization (MOMP). Using this method, cells that are dependent on Bfl-1, overexpress Bfl-1, or have Blf-1-induced resistance to chemotherapeutics will demonstrate increased MOMP (e.g., in comparison to non-cancerous cells or cells that are not Bfl-1 dependent, don't overexpress Bfl-1, or don't have Bfl-1 induced resistance to chemotherapeutics).

In any of the methods described herein, the cells can be permeabilized by permeabilizing agent(s) known in the art, including, for example, digitonin, saponin, or streptolysin, etc. Cells can also be permeabilized by methods, for example, such as electroporation.

The compounds (e.g., compounds comprising the peptides) described herein are particularly useful for diagnosing the dependence of cancer cells on the anti-apoptotic protein Bfl-1, as they are relatively selective and specific for Bfl-1 in comparison to other anti-apoptotic proteins in the Bcl-2 protein family. This can aid in predicting how sensitive a subject will be to a particular chemotherapy treatment or how well a subject will react to a treatment.

The peptides described herein can be used in combination or in tandem with peptides demonstrating selectivity for other Bcl-2 family proteins, e.g., for example, peptides selective for Bcl-$x_L$, Mcl-1, and/or Bcl-2.

As described, the peptides described herein can include a detectable label. The peptides described herein can be conjugated (e.g., attached) to a dye for imaging using any of the methods known in the art for imaging or quantifying a dye, for example, in histology. Peptides conjugated to a dye, as described herein, can be useful, for example, for detecting Bfl-1 expression of a cell, e.g., overexpression of Bfl-1. This can aid in, for example, predicting how well a subject will react to a particular chemotherapy treatment or diagnosing a cancer cell.

EXAMPLES

The invention is further described in the following examples, which do not limit the scope of the invention described in the claims.

Peptidic agents for selective targeting of anti-apoptotic protein Bfl-1 were designed and characterized based on modifications to the PUMA BH3 domain. Resulting peptides were then analyzed for structural interactions with Bfl-1, strength and type of Bfl-1 binding, and selectivity using BH3 profiling.

Example 1: Design and Characterization of Peptide Sequences

Library peptides, the Puma BH3 peptide, and Puma BH3 peptide mutants were 23 residues long with N-terminal acetylation and C-terminal amidation; fluoresceinated Bim BH3 was 18 residues long with N-terminal 5/6-fluorescein amidite and C-terminal amidation; and covalent peptide inhibitors had N-terminal acrylamide and C-terminal amidation. Peptides were synthesized by the MIT (Massachusetts Institute of Technology) Biopolymers Laboratory. The crude synthesis product was purified by HPLC on a C18 column with a linear gradient of acetonitrile in water. Peptides were verified by mass spectrometry.

Amines from natural and unnatural amino acid side chains (e.g. 2,3-diaminopropionic acid, 2,4-diaminobutyric acid, Ornithine, Lysine) could also be modified with acrylamide. Crosslinking can be mediated by other commonly used electrophiles including those disclosed in Shannon and Weerapana (Shannon, D. A. & Weerapana, E. Covalent protein modification: the current landscape of residue-specific electrophiles. *Curr. Opin. Chem. Biol.* 24, 18-26 (2015); incorporated herein in its entirety).

To reduce the enormous space of possible 23-mer sequences to <$10^7$ candidates that could be tested experimentally, computational modeling was used to design focused combinatorial libraries. The challenge was to introduce mutations that eliminate off-target binding without destabilizing Bfl-1 binding. All score-able point mutants of Bim at positions A2-E4 were scored using: (1) a position-specific scoring matrix (PSSM) derived from SPOT peptide array data (PSSMSPOT) and (2) STATIUM, a structure-based statistical potential that previously showed good performance evaluating Bcl-2 protein binding to BH3-like peptides.

Methods and techniques for position-specific scoring matrices based on SPOT array intensities (PSSM¬SPOT) are known in the art. PSSMSPOT scores were normalized to wild-type BIM BH3, as described by Dutta et al (Dutta et al., 2010). The structure-based statistical potential STATIUM was used to predict and score the effect of mutations in BH3 peptides on binding to Bfl-1, Mcl-1, Bcl-$x_L$. The crystal structures used to create the STATIUM models were the same as those used in previous studies: 3MQP (Bfl-1:Noxa) (Guan et al., in press), 3PK1 (Mcl-1:BAX) (Czabotar et al., *J Biol. Chem.*, 286:7123-7131, 2011) and 3108 (Bcl-$x_L$: BIM3aF) (Lee et al., *J. Biol. Chem.*, 284:30508-30517, 2009). STATIUM z-scores were normalized using the score distribution for the human proteome, as described by DeBartolo et al., *PLoS Computational Biol.*, 10:e1003693, 2014.

Substitutions were rated as non-disruptive for Bfl-1 binding if they had either a PSSMSPOT_Bfl-1 score greater than the median score for all mutations across all positions or a ΔSTATIUMBfl-1 score (raw Bim score–raw mutant score) greater than the median for all mutations across all positions.

Substitutions were counted as specific for Bfl-1 over Bcl-$x_L$ or Mcl-1 if PSSMSPOT_KSBcl-2-PSSMSPOT_Bcl-$x_L$/Mcl-1 was greater than 0 or if a STATIUM specificity score corresponding to the difference between Z-scores for a peptide binding to two prosurvival proteins was greater than 0. The STATIUM Z-scores were derived relative to a dataset of ~600,000 genomic peptides.

Mutational scoring identified promising positions for introducing sequence variation. Bfl-1, Bcl-$x_L$ and Mcl-1 were predicted to have distinct residue preferences at conserved hydrophobic positions D3 and A4. Many mutations at position E4 were predicted to be strongly Bfl-1 selective. Mutations at positions A2 and G3 were also predicted to confer Bfl-1 specificity. In native BH3 motifs, these sites are generally occupied by small charged or polar residues that can form hydrogen bonds/saltbridges with Bcl-$x_L$ and Mcl-1 groups that are absent in Bfl-1. Finally, the region around sites E2 and G2 has local structural differences in Bfl-1, Mcl-1 and Bcl-$x_L$.

In-house software was used to select degenerate codons at variable sites that optimized the predicted Bfl-1 binding affinity and specificity and that provided chemical diversity in the resulting library. Libraries were constructed using degenerate codons chosen by a computational optimization protocol. To guide the selection of a set of degenerate codons to consider at each position, we divided residue substitutions into three categories, "preferred", "required", and "disruptive". "Preferred" substitutions were those that scored higher than the median of all point mutants of BIM at positions 2α-4e on either PSSMSPOT_Bfl-1 or STATIUM Bfl-1. Additionally, some substitutions that did not meet these criteria but had large specificity scores from either PSSMSPOT or STATIUM for Bfl-1 were included. "Required" substitutions, designated manually, were a subset of the most promising preferred residues, particularly those predicted to be highly selective for Bfl-1 or BIM/PUMA wild-type residues. Specificity for Bfl-1 over $Bclx_L$ or Mcl-1 was determined by the difference of PSSMSPOT scores or the difference in STATIUM z-scores. "Disruptive" residues included mutations with PSSMSPOT or STATIUM scores for Bfl-1 that were more than 1 standard deviation worse than wild type Bim. Degenerate codons selected for consideration encoded all of the required residues. Codons were further selected by prioritized codons based on number of preferred residues included and eliminating any codon that encoded disruptive substitutions.

The degenerate codon combinations were optimized with integer linear programming, as previously described. The library was limited to include at most $1 \times 10^7$ DNA sequences. Codons that encoded 3 or fewer variants were discarded decrease the likelihood that a large percentage of the library would be "poisoned" by a disruptive substitution that wasn't identified by our models. The final library contained a large number of unique protein sequences ($6.84 \times 10^6$) and was enriched in sequences predicted to have high affinity for Bfl-1 and weaker binding than Bim to Mcl-1 and $Bcl-x_L$ on the PSSMSPOT and STATIUM models. As a control, similarly sized libraries were designed to be selective for $Bcl-x_L$ and Mcl-1.

A variety of the point mutants in Puma BH3 is shown in FIG. 1A-C, FIG. 7 and FIG. 8. Point mutations at positions A2-E4 were evaluated as described, to predict mutations in Puma BH3 that could contribute to Bfl-1 selective binding (bold). The PSSM derived from SPOT array mutational data and the STATIUM based analysis of the crystal structure of Bim bound to Bfl-1 (2VM6), Mcl-1 (2PQK), and $Bcl-x_L$ (3FDL) are seen in FIG. 3A and FIG. 3B.

Structural Analysis

To analyze the structural interactions between the peptides and Bfl-1, crystals of various complexes were grown and diffraction data collected. Crystals of Bfl-1 in complex with PUMA, FS2, or F52-1fX peptides were grown in hanging drops over a reservoir containing 1.8 M ammonium sulfate, 0.1 M IVIES pH 7.0 at room temperature. Crystals were seeded with drops containing parent crystals grown in higher ammonium sulfate (2.2-2.4 M) using a cat whisker. The protein was concentrated to 4 mg/ml in 20 mM Tris, 150 mM NaCl, 1% glycerol, 1 mM DTT, pH 8.0 and mixed with peptide at a 1:1 molar ratio. The hanging drops contained 1.5 μl of complex mixed with 1.5 μl of reservoir solution. Crystals were cryo-protected by transferring into 2.0 M lithium sulfate with 10% glycerol prior to flash freezing. Diffraction data were collected at the Advanced Photon Source at the Argonne National Laboratory, NE-CAT beamline 24ID-C. The Bfl-1:FS2 data were integrated and scaled to 1.2 Å using HKL2000 and phased using a rigid body alignment with chain A of structure 4ZEQ using PHENIX. The peptide was built into the difference density from the rigid body refinement and the structure was refined with iterative rounds of refinement and model building using PHENIX and COOT. The PUMA and FS2_1fX complex data sets extended to 1.33 A° and 1.73 A°, respectively, and were phased with the Bfl-1 chain of the FS2 complex model.

Crystals of the Mcl-1/F52 peptide complex were grown at room temperature in hanging drops over a reservoir containing 0.2 M zinc sulfate, 0.1 M imidazole (pH 6.5), and 3% 6-aminohexanoic acid. The protein was mixed with peptide at a 1:1 molar ratio and diluted to 2 mg/ml in 20 mM Tris, 150 mM NaCl, 1% glycerol, 1 mM DTT, pH 8.0. The hanging drops contained 1.5 mL of complex mixed with 1.5 mL of reservoir solution. Crystals were cryoprotected by transferring into 15% glycerol, 0.2 M zinc sulfate, 0.1 M imidazole (pH 6.5) and 3% 6-aminohexanoic acid prior to flash freezing. Diffraction data were collected at the Advanced Photon Source at the Argonne National Laboratory, NE-CAT beamline 24-ID-E. The data were processed to 2.35 A° and phased using molecular replacement with chain A of structure 3PK1 using PHASER and refined using PHENIX and COOT.

Figures 1A, 1B:
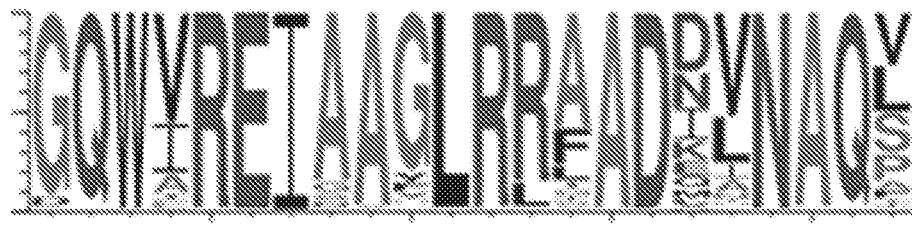
FIG. 1A-E show that epistatic mutations in PUMA confer Bfl-1 binding specificity.
Figures 1C, 1D:
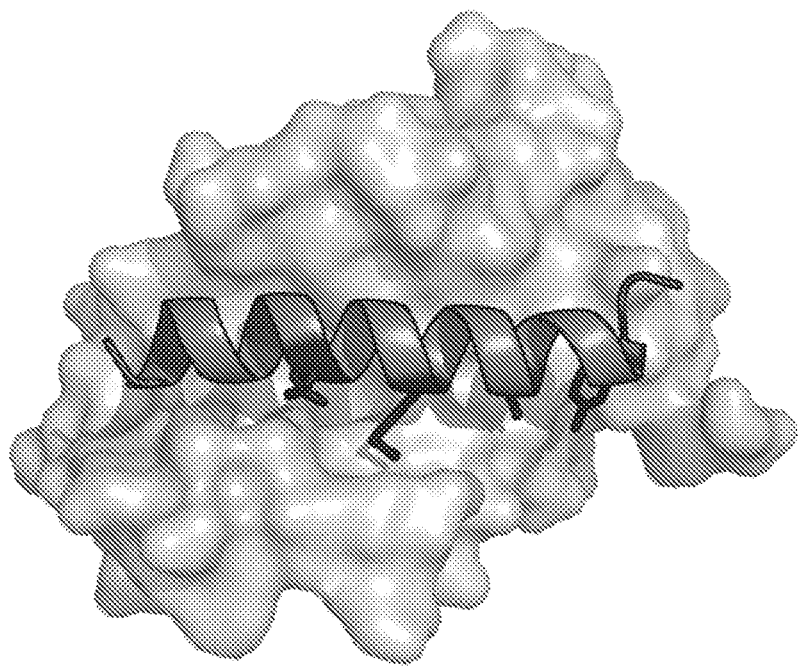

A crystal structure of PUMA bound to Bfl-1 is shown in FIG. 1D. Seven positions in the Puma BH3 domain that make significant interactions with Bfl-1 were selected as potentially favoring binding to Bfl-1 over Mcl-1 and $Bcl-x_L$, and were subsequently mutated.

FS1, FS2 and FS3 included mutations to larger residues than those in PUMA at their N-termini (FIG. 1C (bold)), and smaller residues at their C-termini (FIG. 1C (underlined)). Deep sequencing of additional selective sequences supported this trend: Of 612 unique peptide sequences from the final round of sorting that originated from the Bfl-1 targeted library sequences, 364 showed this type of residue size patterning at the same sites (FIG. 1A).

Figure 1E:
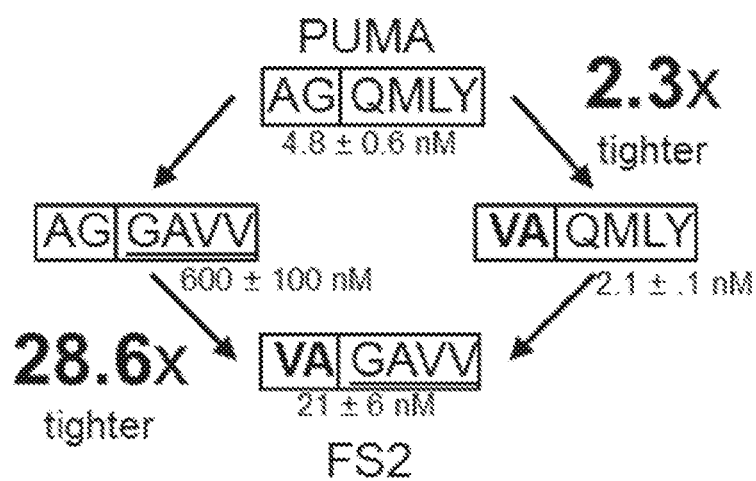

To assess whether the combination of large and small residues played a role in establishing binding specificity, PUMA/FS2 chimeric peptides were tested for binding to all five anti-apoptotic proteins. Mutating PUMA to introduce smaller residues at positions G2, D3, A4 and E4 differentially impaired binding to all receptors and resulted in weak yet specific binding to Bfl-1. Mutating residues at the N-terminus of PUMA to larger residues at positions A2 and E2 gave a modest 2.3-fold increase in affinity for Bfl-1. But the same mutations in the context of smaller residues at positions G2, D3, A4 and E4 improved affinity for Bfl-1 by 28.6-fold (FIG. 1E). The different effects of these mutations, when made in different contexts, indicates an energetic coupling consistent with a structural repositioning of the designed peptides in the groove of Bfl-1.

To better understand the structural basis for the epistasis, the X-ray crystal structures of Bfl-1 bound to PUMA, at 1.33 A° resolution, and of Bfl-1 bound to FS2 at 1.2 A° resolution, were solved. FIG. 4A-E shows the binding of FS2, a Bfl-1 specific peptide, and PUMA to Bfl-1. As shown in FIG. 4A, PUMA and FS2 each adopt new, distinct positions in the binding groove, as compared to available X-ray structures of other BH3 peptides bound to human or murine Bfl-1. FS2 is shifted 1.2 A° and rotated 17° in the binding groove compared to its parent peptide PUMA. FIG. 4B shows that the peptide C-terminus, which harbors the large-to-small mutations (open circles), is repositioned more dramatically than the N-terminus. Despite the shifts in peptide binding geometry, the structures of Bfl-1 in these newly solved complexes are highly similar. The all-atom RMSD for residues in the binding pocket (within 5 A° of the BH3 peptide) of Bfl-1:FS2 vs. Bfl-1:PUMA is <0.7 A° and is 1.05 A° for Bfl-1:FS2 vs. Bfl-1:BIM.

The slightly different orientation of the FS2 BH3 domain, as compared to PUMA, may contribute to its selectivity to Bfl-1. Further structural analysis showed that the Bfl-1:FS2 complex supports several key side-chain interactions that are absent in Bfl-1:PUMA and that may be important for selective binding. Surprisingly, aspartate at position F3 (D3f) in FS2, which is strongly conserved in known BH3 motifs, makes different interactions than what is observed in numerous previously solved Bcl-2 complex structures. FIG. 4C shows that D3f typically forms a salt bridge with arginine 88 (R88) in helix four in Bfl-1 or the corresponding arginine in Bcl-$x_L$, Mcl-1, Bcl-w or Bcl-2. In the Bfl-1:FS2 structure, the carboxylate of D3f is shifted 5.6 A° away from the guanidinium group of R88, and is highly solvent exposed (FIG. 4C). Because D3f does not form the canonical D3f R88 interaction and is solvent exposed, FS2 should be expected to tolerate mutations at this site. This was confirmed by the tight binding of six peptides with alanine, serine, asparagine, glutamate, histidine or tyrosine at this position. Disruption of the D3f R88 salt bridge would be expected to reduce affinity for Bfl-1 and for all of the other anti-apoptotic receptors. However, as shown in FIG. 4E, this change may be partially compensated in the Bfl:FS2 complex by hydrogen bonding on the opposite side of the FS2 helix between arginine at position 3c (R3c) of FS2 and asparagine 51 (N51) of Bfl-1. In Bfl-1:FS2, position C3 is positioned closer to helix 2 of Bfl-1 than in Bfl-1:PUMA, allowing R3c (position C3) to fill the space left by an adjacent methionine-to-alanine mutation at D3 when it adopts this hydrogen-bonded position. N51 at this position of helix two is unique to Bfl-1 among the human anti-apoptotic proteins.

Other structural differences between PUMA and FS2 binding are apparent near the N-terminal end of the peptide. Modeling FS2 mutations in the Bfl-1:PUMA structure suggested that the small-to-large mutation of alanine at position 2A in PUMA to the valine in FS2 would result in steric clashes with helix 4 of Bfl-1 for all backbone-dependent rotamers. This change is accommodated by the shift in the Bfl-1:FS2 structure. Also, FIG. 4D shows that a rotation of FS2 in the Bfl-1 binding groove partially buries the phenylalanine at position G1 that is solvent-exposed in the PUMA complex, which may be energetically favorable.

Because the altered binding mode of FS2 is expected to impact predictions made using structure-based models, we re-scored the designed Bfl-1 library on the shifted Bfl-1:FS2 structure using STATIUM. FS1 and FS2 scored much better (higher) on the shifted model than on the original model, whereas PUMA scored better on the original model. Analysis of the entire pool of sequences that passed screening showed that these peptides were enriched in sequences that scored better on the shifted model, compared to the input library, consistent with our observation of size patterning in the majority of these sequences.

Structural Basis of Off-Target Binding to Mcl-1

To better understand the structural basis of FS2-binding specificity, the X-ray crystal structure of FS2 bound to Mcl-1 at 2.35 A ° resolution was solved. FS2 binding to Mcl-1 is >100 fold weaker than binding to Bfl-1. As shown in FIGS. 5A-B, similar to the way FS2 binds to Bfl-1, FS2 engages Mcl-1 in a shifted orientation relative to BIM. FIG. 5C shows that this shift re-positions the highly conserved aspartate at peptide position 3f to a location 4.8 A ° away from Mcl-1, disrupting the canonical salt bridge with arginine 92, as is the case for FS2 binding to Bfl-1. This disruption would be expected to reduce affinity for Mcl-1, but it doesn't account for the specificity of FS2 for Bfl-1, because the salt bridge is lost in both complexes. There are other differences between the Bfl-1:FS2 and Mcl-1:FS2 structures that may account for some of the affinity difference. For example, FIG. 5D shows that R3c in FS2 forms a hydrogen bond with N51 of Bfl-1, but does not form an equivalent interaction with Mcl-1 and is instead solvent exposed. In Mcl-1, there is an alanine (A55) at this site, and an adjacent histidine (H53) would be expected to clash with R3c if it adopted this conformation. FIG. 5E shows that the N-terminus of FS2 is also buried further into the binding groove of Bfl-1 than Mcl-1. The Bfl-1 binding groove is wider in this region than the Mcl-1 binding groove when many Bfl-1 and Mcl-1 structures are aligned. This region of the groove is formed by helices 3 and 4. There is an amino acid insertion in the loop between helices 3 and 4 that is unique to Bfl-1 that likely contributes to the distinct structural environment of Bfl-1 in this region.

Binding Assay & Results

Fluorescence polarization assays were performed in order to measure the binding abilities of the peptide constructs. Competition fluorescence polarization experiments were performed by titrating 10-0 μM of unlabeled peptide into 50 nM receptor with 25 mM fluorecinated Bim (fluorescein-IWIAQELRRIGDEFNAYY) in FP buffer (25 mM Tris pH 7.8, 50 mM NaCl, 1 mM EDTA, 0.001% v/v Triton-X, 5% DMSO). C-myc-tagged receptors were used for all Bcl-2 homologs. Plates were mixed at room temperature for 3 h. Experiments were done in triplicate. Data were fit, as described for competition fluorescence anisotropy experiments in Foight et al. (Foight, G. W., Ryan, J. A., Gullá, S. V, Letai, A. & Keating, A. E. Designed BH3 Peptides with High Affinity and Specificity for Targeting Mcl-1 in Cells. *ACS Chem. Biol.* 9, 1962-8 (2014)), to a complete competitive binding model (equation 17 in Roehrl et al., 2004) (Roehrl, M. H. A., Wang, J. Y. & Wagner, G. A General Framework for Development and Data Analysis of Competitive High-Throughput Screens for Small-Molecule Inhibitors of Protein-Protein Interactions by Fluorescence Polarization†. *Biochemistry* 43, 16056-16066 (2004)) using a Python script.

Ki values were obtained from the competition assays with fluoresceinated Bim peptide. FS1, FS2, and FS3 bound selectivity to Bfl-1 over other Bcl-2 family proteins (Ki±standard deviation of four replicates). These data suggest that FS1, FS2, and FS3 competitively inhibit Bim binding to Bfl-1.

The binding data of various peptide constructs obtained from competition assays with fluoresceinated Bim peptide are shown in FIG. 7 and FIG. 8. FS1, FS2, and FS3 bound selectivity to Bfl-1 over other Bcl-2 family proteins (Ki±standard deviation of four replicates). These data suggest that FS1, FS2, and FS3 competitively inhibit Bim binding to Bfl-1 and that Y4 eV modestly contributes to Bfl-1 specificity but is somewhat disruptive for Bfl-1 binding.

BH3 Profiling Assay & Results

A whole-cell BH3 profiling assay was used to test the specificity of the peptide constructs in several cell lines with known dependencies on anti-apoptotic proteins, including Bcl-2, Mcl-1, Bcl-$x_L$, or Bfl-1. The creation and characterization of the BCR-ABL-expressing B-lineage acute lymphoblastic leukemia suspension cell lines with engineered dependencies on human versions of anti-apoptotic genes is detailed in Koss et al., *Oncotarget,* 7:11500-11511, 2016. Cells were grown in RPMI (Life Technologies, Carlsbad, Calif.) with 10% fetal bovine serum, 2 mM L-glutamine, 10 mL/L 100× Pen/Strep (Life Technologies #15140122), 25 mM HEPES and 10 mL/L 100×NEAA (Life Technologies, 11140050). The adherent cell lines PC-3 (RRID: CVCL_0035) and SF295 (RRID: CVCL_1690) are from the NCI60 panel (Lorenzi et al., 2009) and were grown in RPMI (Life Technologies) with 10% fetal bovine serum, 2 mM L-glutamine and 10 mL/L 100× Pen/Strep (Life Technologies #15140122). Cell line identities were confirmed by STR profiling. The Lookout *Mycoplasma* PCR detection kit (Sigma) was used to detect *mycoplasma* infection. *Mycoplasma* was only detected in the PC-3 cell line, and internal controls were used to account for this phenotype.

Peptides were titrated by serial dilution in MEB buffer (150 mM Mannitol, 10 mM HEPES-KOH pH 7.5, 50 mM KCl, 0.02 mM EGTA, 0.02 mM EDTA, 0.1% BSA and 5 mM Succinate) containing 20 mg/mL oligomycin, 50 mg/mL digitonin, 2 mM JC-1 and 10 mM 2-mercaptoethanol in 384-well plates. Controls for no depolarization (1% DMSO) and complete depolarization with the mitochondrial oxidative phosphorylation uncoupler FCCP (20 mM) were included for data normalization. Cells were suspended at 1.67×106 cells/mL in MEB. 15 mL of cell suspension was added to each well containing 15 mL of treatment solution. Fluorescence emission was measured every 5 min for 3 hours at 590 nM with 525 nM excitation on a Tecan Safire2. To produce percent depolarization, the area under the resultant curve was calculated and normalized to the assay controls. Peptide titration curves were fit to sigmoidal dose-response curves using Graphpad PRISM seven to obtain $EC_{50}$ values.

As depicted in FIG. 9A, in this assay, permeabilized cells were contacted with increasing doses of the BH3 peptides, and mitochondrial outer membrane permeabilization (MOMP) was monitored using a voltage-sensitive dye (JC-1). The apoptotic sensitivity of BCR-ABL-expressing B-lineage acute lymphoblastic leukemia (B-ALL) cell lines engineered to depend on Bcl-2, Bcl-$x_L$, Mcl-1 or Bfl-1 overexpression for survival. FIG. 9B shows the depolarization of mitochondria induced by designed peptides in four cell lines that depend on ectopic expression of Mcl-1 (M), Bcl-2 (2), Bcl-$x_L$(X), or Bfl-1(F) for survival. In comparison with a shorter, truncated PUMA BH3 (PUMA1e-4c, PUMAsh), which promoted mitochondrial depolarization in all of the cell lines tested, at 100 nM the Bfl-1 selective inhibitors FS1, FS2 and FS3 promoted depolarization only in Bfl-1 dependent cells. An inactive PUMAsh mutant, PUMA L3aA; D3fA (PUMA 2A) was used as a negative control (Ryan and Letai, *Methods*, 61:156-164, 2013). As shown in FIG. 9C, $EC_{50}$ values for inducing mitochondrial permeabilization in the engineered cell lines agreed well with trends in Bfl-1-binding affinities, as expected based on the mechanism of action.

As an additional test for on-pathway activity, cytochrome c release was measured in the same engineered cell lines in response to peptide treatment, using iBH3 profiling (see Ryan et al., *Biol. Chem.*, 397:671-678, 2016). Cells were suspended in MEB buffer (150 mM mannitol, 50 mM KCl, 10 mM HEPES, 5 mM succinic acid, 20 mM EGTA, 20 mM EDTA, 0.1% BSA, final pH 7.4) at 0.5*106 cells/mL (adherent lines) or 2*106 cells/mL (suspension lines). Cell suspension was added to a 384 non-binding well plate (10 mL/well) containing peptides at 2× final concentration in MEB with 20 mg/mL digitonin. Plates were incubated at 25° C. for 1 hour. To terminate exposure, 10 mL of 4% formaldehyde in PBS was added to each well, plates were incubated for 10 minutes before addition of 10 mL N2 buffer (1.7 M Tris, 1.25 M glycine, pH 9.1) for 5 min. 10 mL of staining buffer (2% Tween20, 10% BSA, PBS) containing 10 mg/mL Hoechst 33342 and 1.25 mg/mL anti-cytochrome c Alexa647 conjugate (BioLegend clone 6H2.B4) was added to each well before sealing the plate and shaking overnight. The median fluorescence of the cytochrome c channel of Hoechst positive singlets was recorded by an IntelliCyt iQue Screener Plus. Cytochrome c release was determined by normalizing the median fluorescence intensity (MFI) data to positive control wells (Alamethicin) and negative control wells (DMSO) as follows: Cytochrome release=1−(MFI$_{sample}$−MFI$_{Alamethicin}$)/(MFI$_{DMSO}$−MFI$_{Alamethicin}$)

The specificity pattern observed when monitoring cytochrome c release was consistent with that obtained by BH3 profiling read out using JC-1 (FIG. 9D). A Mcl1 selective peptide, MS1 was used as a control (see Foight et al., *Methods Mol. Biol.* 1561:213-232, 2014). In both assays, FS3 promoted mitochondrial depolarization more potently than FS1 or FS2, but was less selective, with significant cross reactivity at 30 mM peptide concentration.

These data demonstrate that each of FS1, FS2, and FS3 preferentially antagonize Bfl-1 function to promote mitochondrial outer membrane permeabilization, a defining feature of the intrinsic apoptotic pathway.

Example 2: Design and Characterization of Covalent Inhibitors of Bfl-1 with Enhanced Specificity Structural Analysis The initial sorts for Bfl-1 selective binders, as described in Examples 1 and 3, identified many sequences that included cysteine at position G1 or B2. Cysteines encoded at several other positions along the BH3 motif were not enriched. Furthermore, cysteine was not enriched in previous screens for Bfl-1 binding. This observation led to the hypothesis that Bfl-1 binding selectivity could be improved in non-reducing conditions if the peptide ligand formed a disulfide bond with cysteine 55 (C55) of Bfl-1, which is adjacent to the binding cleft of Bfl-1 and unique to Bfl1 among Bcl-2 family paralogs (see FIG. 10A). Because this cysteine is structurally unique to Bfl-1, acrylamide and other electrophilic groups can be used to modulate Bfl-1 targeting. This strategy can be generally applied to improve a broad range of Bfl-1 targeting molecules (peptides or small molecules), using acrylamide or other electrophilic groups with reactivity tuned to achieve selective binding. See, e.g., FIG. 11.

Testing yeast-displayed peptides for binding to a Bfl-1 cysteine-to-serine (C55S) mutant confirmed that PUMA and BIM bound to Bfl-1 C55S, whereas the majority of the peptides in the cysteine-enriched pool bound to wild-type Bfl-1 but not to Bfl-1 C55S. Rescreening the library using Bfl-1 C55S led to the identification of FS1, FS2 and FS3, as described herein. In addition, the discovery that BH3 peptides in the library could access a unique, reactive cysteine in Bfl-1 led to the design covalent inhibitors based on these peptides.

Structure-based modeling was used to choose appropriate cysteine-reactive electrophiles and optimize their placement in different BH3 positions in the 2VM6 structure of Bfl-1 bound to BIM BH3 (see Herman et al., *FEBS Lett*, 582: 3590-3594, 2008). As shown in FIGS. 10B-C, the two most promising designs featured N-terminal Michael acceptors at position G1 (FS2_1gX) or F1 (FS2_1fX) of peptide FS2. These designs were tested for covalent modification of Bfl-1 and Bfl-1 C55S using gel-shift assays. Both FS2_1gX and FS2_1fX modified Bfl-1 once or less when applied at micromolar concentrations, whereas Bfl-1 C55S (which contains two other solvent-exposed cysteine residues) did not react with these electrophilic peptides for at least 6 hours. Densitometry was used to measure the fraction of Bfl-1 reacted as a function of time for both designs. As shown in FIG. 10D, FS2_1fX reacted with Bfl-1 with a half-life of 6.5 min and FS2_1gX reacted more slowly with a half-life of 138 min.

As shown in FIG. 10E, FS2_1fX was tested in BH3 profiling and found to improve on-pathway targeting of Bfl-1 compared to N-terminally acetylated control and was selective for Bfl-1. FS2_1fX was more potent than FS2_1fAc in BH3 profiling assays of Bfl-1 dependent cells. Data are mean±SD of 3 or more independent measurements. BH3 profiling assay was performed as previous described using the modified peptides and BCR-ABL-expressing B-lineage acute lymphoblastic leukemia (B-ALL) cell lines that depend on ectopic expression of Bcl-2, Bcl-$x_L$, Bfl-1, or Mcl-1 for survival. FIGS. 12A-B depict similar data for FS2gX and FS2gAc. These data demonstrate that electrophiles, e.g., as found in FS2_1fX, can selectively increase potency against Bfl-1 relative to comparable peptides without electrophiles, e.g., FS2_1fAc, to promote mitochondrial outer membrane permeabilization, a defining feature of the intrinsic apoptotic pathway.

As shown in FIGS. 10F-G, a crystal structure of FS2_1fX bound to Bfl-1 was solved that showed clear electron density consistent with a covalent bond to C55, as designed.

Example 3: Library Construction and Screening

Oligonucleotides encoding the peptide libraries designed to be specific for Bfl-1, Bcl-$x_L$ and Mcl-1 were synthesized in the context of BIM and PUMA BH3 sequences. Pooled BIM-based libraries and pooled PUMA-based libraries were then screened separately for tight and selective binding to Bfl-1. Screening the libraries designed for Mcl-1 and Bcl-$x_L$ for binding to Bfl-1, in addition to the library designed to target Bfl-1, provided an opportunity to evaluate the utility of computational library focusing.

Construction of the Yeast-Display Vector and the Combinatorial Library

The BH3 peptide library was constructed using homologous recombination in yeast using wild-type Puma-BH3 as a template. Puma-BH3 (residues 132-172 from human Puma, UniProt #Q9BXH1-1) was subcloned into the plasmid pCTCON2 with a carboxy-terminal FLAG tag and amino-terminal HA tag. Flanking BamH1 and XhoI sites were used to subclone into the plasmid pCTCON2 to fuse Puma-BH3 to the C terminus of Aga2p with a (Gly$_4$-Ser)$_3$ linker. The Puma-BH3 library was constructed with PCR using primers with degenerate bases (forward primer: 5' CGGATCCGGTGGCCAATGGVHACGTGAAAT

TKVTGCCNDCCTGCGTCGCNBCGCGGATVWKNHTAATGCCCAANYTGAAC

GTCGTCGCCAGGAGGAAC 3').

The PCR product was further amplified until there was at least 40 bp of homology to the acceptor vector on both ends of the library inserts. The pCTCON2 acceptor vector was cleaved with XhoI and NheI, gel purified, and transformed along with the extended PCR product into yeast following the procedure of Gietz et al. (Gietz, R. D. & Woods, R. A. Transformation of yeast by lithium acetate/single-stranded carrier DNA/polyethylene glycol method. *Methods Enzymol.* 350, 87-96 (2002). 20 electroporations produced a total of 5.22×10$^8$ transformants with vector background estimated at <0.01%. DNA from transformed cells was PCR amplified to check for randomization.

Flow Cytometric Analysis and Sorting

Yeast-surface display was used to identify selective Bfl-1-binding peptides from the mixed libraries. FIG. 2A depicts the yeast-surface display configuration, in which BH3 peptides were expressed as fusions to Aga2, and HA tag expression was detected with APC and Bfl-1 binding was detected with PE.

The yeast-displayed Bfl-1 library was grown and sorted using FACS based on a protocol that was adapted from Reich et al (Reich, L. 'Luther', Dutta, S. & Keating, A. E. in 233-247 (2016). doi:10.1007/978-1-4939-3569-7_14). Glycerol stocks were used to inoculate SD+CAA to a final OD$_{600}$ of 0.05 in SD+CAA in a volume sufficient to oversample the estimated library diversity by at least 10-fold and grown for 12 h at 30° C. Cells were diluted to OD$_{600}$ of 0.005-0.01 in SD+CAA and grown to OD$_{600}$ of 0.1-0.6 (~12 h) at 30° C. To induce expression, cells were diluted into SG+CAA (40 mL inoculate/L SG+CAA) and grown to OD$_{600}$ of 0.2-0.5 (16-24 h) at 30° C. Induced yeast cells were filtered with 0.45 µm filter plates or bottle-top filters and washed twice with BSS (50 mM Tris, 100 mM NaCl, pH 8, 1 mg/ml BSA). Sufficient cells to oversample the library diversity were resuspended in BSS with at least 10× molar excess ligand and incubated for 2 h at 21° C. with gentle shaking. Cells were filtered, washed twice in chilled BSS, and incubated with a mixture of primary antibodies (anti-HA mouse, Roche, and anti-c-myc rabbit, Sigma) at 1:100 dilution in a volume of 20 µl per 10$^6$ cells for 15 min at 4° C. in BSS. Cells were filtered, washed twice in chilled BSS, and incubated in a mixture of secondary antibodies (1:40 APC rat anti-mouse, BD, and 1:100 PE goat anti-rabbit, Sigma) in BSS at 4° C. in the dark for 15 min. The filtering and washing steps were repeated and the labeled cells were resuspended in BSS and analyzed on a BD FACSCanto flow cytometer or sorted on a BD FACSAria using FACSDiva software. The sorted cells were collected in selective media containing glucose (SD+CAA) and grown to an OD$_{600}$ of 6-10 for ~48 hours in the presence of streptomycin/penicillin to prevent bacterial growth, pelleted, washed, and stored as glycerol stocks.

A series of positive, negative, and completion sorts were used to enrich in Bfl-1 selective binders as follows: 1) positive sort with 100 nM c-myc-Bfl-1 (top ~5% binders collected and frozen to make glycerol stocks), 2) negative sort with a mixture100 nM c-myc-Mcl-1, c-myc-Bcl-$x_L$, c-myc-Bcl-2, and c-myc-Bcl-w (bottom ~10% of events observed were collected), 3-5) series of competition sorts with a mixture of 100 nM c-myc-Bfl-1 and 1 µM each of orthogonally labeled Mcl-1, Bcl-$x_L$, Bcl-2, and Bcl-w (top ~5-10% of cells were collected), 6) a increasingly stringent competition sort with a mixture of c-myc-Bfl-1C55S (10 nM) and 1 µM each of orthogonally labeled Mcl-1, Bcl-$x_L$, Bcl-2, and Bcl-w (top ~5% of cells were collected). To estimate the library diversity, we sequenced 48 clones each from pools 5 and 6. We found the library to be enriched in sequences with cysteine mutations at the N-terminus of the BH3 domain. We repeated sorts 5 and 6 with the Bfl-1 point mutant c-myc-Bfl-1C55S to identify peptides whose binding doesn't rely on disulphide bond formation. From the second sorting attempt, we sequenced 48 clones each from pools 5' and 6'.

As shown in FIG. 2B, FACS analysis revealed that the initial libraries had a modest number of cells expressing peptides that bound to Bfl-1 at 100 nM. Only ~5% of cells in the unsorted PUMA libraries bound to Bfl-1 at 100 nM. This is consistent with predictions that less than 6.5% or 4% of the theoretical library would bind as well or better than PUMA, according to PSSMSPOT or STATIUM, respectively.

FIGS. 2C-G show that most of the peptides that bound Bfl-1 were cross-reactive with one or more other Bcl-2 family proteins. This cross-reactivity was expected based on the high correlation of predicted binding scores for Bfl-1, Mcl-1 and BclxL and highlights the challenge of identifying specific binders. Six rounds of positive, negative and/or competition FACS screening were used to isolate cells that expressed the tightest and most Bfl-1-selective peptides. Mcl-1, Bcl-$x_L$, Bcl-2 and Bcl-w were included in the screen as untagged competitors. Early screening provided many Bfl-1 selective hits from the PUMA libraries, but few from the BIM libraries, so the BIM libraries were not pursued. FIG. 2H shows that after several rounds of competition screening, the PUMA library was enriched in cells displaying peptides that bound to Bfl-1 (Myc-tagged Bfl-1) at 100 nM in the presence of 40-fold excess unlabeled competitor (Mcl-1, Bcl-2, Bcl-w, and Bcl-$x_L$).

Fifty colonies isolated in the final round of screening were sequenced, providing 13 unique sequences: nine sequences were from the Bfl-1 specific library, two were from the Bcl-$x_L$ library, and two were from the Mcl-1 library. We tested three Bfl-1 selective peptides that were recovered two or more times (FS1, FS2 and FS3). FS1, FS2 and FS3 were all derived from the Bfl-1 targeted library, although FS1 also contained one mutation caused by a spurious single-base pair mutation. As shown in FIG. 2I, FS1, FS2 and FS3 each had reduced affinity for Bfl-1 relative to PUMA, but significantly increased specificity. FS1 bound Bfl-1 with Ki=15 nM and at least 150-fold specificity for Bfl-1 relative to Bcl-$x_L$, Bcl-2, Bcl-w and Mcl-1.

Evaluation of Library Design

To analyze enrichment trends and to assess the success of our library design, samples from the naive pool and from pools collected after 3, 4, 5 and 6 rounds of sorting were deep sequenced. The naive pool was diverse and not dominated by any particular subset of sequences. In contrast, FS1 (38% of sequences, the most prevalent library member), FS2 (25% of sequences), and many other peptides from the Bfl-1 targeted library were prominent in the final screening pool. Analysis of sequential pools showed that peptides from the Bfl-1 targeted library were substantially enriched relative to peptides from the Bcl-$x_L$ and Mcl-1 targeted libraries. Of the unique sequences in the final pool, 73.9% were from the Bfl-1 targeted library.

Peptides from the Bfl-1 targeted library that passed all rounds of screening with the STATIUM and PSSMSPOT models used in library design were scored. Most sequences were predicted to have improved selectivity for Bfl-1 relative to PUMA (98-99% with improved specificity over Bcl-$x_L$ or Mcl-1 by PSSMSPOT, and 95% or 62% with improved specificity over Bcl-$x_L$ or Mcl-1, respectively, by STATIUM). The selected sequences were not among those predicted by either model to be the tightest or most Bfl-1 selective in the theoretical library.

Illumina Sequencing and Data Processing

Glycerol stocks from each pool were grown ON in SD+CAA, using sufficient stock to oversample the estimated library diversity by at least 10-fold. $1 \times 10^8$ cells from each pool were pelleted in a microcentrifuge tube at 300×g for 1 min and washed twice with PBS. The plasmid DNA from yeast was extracted using the Zymoprep™ Yeast Plasmid Miniprep II (Zymo Research) reagents and Qiagen miniprep column. The DNA was eluted in water. The BH3 library was amplified with PCR using primers that encoded an MmeI restriction enzyme site at 5' end and a universal Illumina sequencing region on the 3' end. After purification with the Qiagen PCR purification, the PCR products were digested with MmeI (3.45 pmol DNA:2 µL MmeI, NEB) for 1 h at 37° C. before being heat inactivated at 80° C. for 20 min. Each digestion product was then ligated with T4 DNA ligase (NEB) to double-stranded DNA fragments containing Illumina adapters with an adapter containing a unique barcode for 30 min at 20° C. and heat inactivated for 10 min at 65° C. Barcodes were varied by at least two bases and were used assign Illumina reads to its pool. A final PCR amplified the ligation product and extended the 5' and 3' regions to include adaptor sequences for Illumina sequencing. Samples were then multiplexed and run in one lane on an Illumina Nextseq with paired-end reads of 75 bp using the universal Illumina forward sequencing primer and a Puma construct specific Illumina read primer reverse (5' CGCCTTGTTCCTCCTGGCGACGACGTTCATAT-TGGGC 3').

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound comprising a peptide comprising the amino acid sequence:

F1 G1 A2 B2 C2 D2 E2 F2 G2 A3 B3 C3 D3 E3 F3 G3 A4 B4 C4 D4 E4 F4 G4 (SEQ ID NO:1), wherein:
F1 is Q or is missing;
G1 is W, G, 4, 4-biphenylalanine, azidoalanine, or is missing;
A2 is A, V, or I;
B2 is R;
C2 is E, H, or 2,3-diaminopropanoic acid;
D2 is I, norleucine, homoleucine, cyclohexylalanine, 2-aminoheptanoic acid, or 2,4-diaminobutyric acid;
E2 is G, or A;
F2 is A or Y;
G2 is Q, G, D, or E;
A3 is L, cyclohexylalanine, or homoleucine;
B3 is R;
C3 is R, or L;
D3 is M, A, F, d-phenylglycine, d-histidine, d-leucine, α-aminoisobutyric acid, or cyclohexanecarboxylic acid;
E3 is A, ornithine, 2,4-diaminobutyric acid, or 2,3-diaminopropanoic acid;
F3 is D or homoglutamate;
G3 is D, N, I or a conservative substitution;
A4 is L, V, or d-cyclohexylalanine;
B4 is N;
C4 is A;
D4 is Q;
E4 is Y, L, or V;
F4 is E;
G4 is R;
provided that A2, E2, G2, C3, D3, G3, A4 and E4 are not simultaneously A, G, Q, R, M, D, L and Y respectively.

2. The compound of claim 1, wherein F1 is Q or is missing; G1 is W, G, or is missing; A2 is V or I; B2 is R; C2 is E, H, or 2,3-diaminopropanoic acid; D2 is I or 2,4-diaminobutyric acid; E2 is A; F2 is A or Y; G2 is G, D, or E; A3 is L; B3 is R; C3 is L or R; D3 is A or F; E3 is A; F3 is D; G3 is N, D or I; A4 is L or V; B4 is N; C4 is A; D4 is Q; E4 is L or V; F4 is E; and G4 is R.

3. The compound of claim 1, wherein an electrophilic group is attached to the N-terminus of the peptide via an amide bond.

4. The compound of claim 3, wherein the electrophilic group is an acrylamide.

5. The compound of claim 1, wherein A2 is V, E2 is A, G2 is G, C3 is L, D3 is A, G3 is N, A4 is V and E4 is L.

6. The compound of claim 1, wherein A2 is V, E2 is A, G2 is G, D3 is A, A4 is V and E4 is V.

7. The compound of claim 1, wherein A2 is I, E2 is A, G2 is G, D3 is F, G3 is I and E4 is V.

8. The compound of claim 4, wherein an acrylamide is attached to the amino terminus of the polypeptide via an amide bond.

9. The compound of claim 1, wherein a cell penetrating peptide tag or an affinity tag is attached to the peptide.

10. A compound comprising a peptide comprising an amino acid sequence selected from:

QWAREIGAQLRRIVIADDLNAQVER; (SEQ ID NO: 6)

QWVREIAAGLRRAADDVNAQYER; (SEQ ID NO: 7)

QWVREIAAQLRRIVIADDLNAQYER; (SEQ ID NO: 8)

QWAREIGAGLRRAADDVNAQVER; (SEQ ID NO: 9)

GVREIAYGLRRAADDVNAQVER; (SEQ ID NO: 10)

GVRHIAYGLRRAADDVNAQVER; (SEQ ID NO: 11)

GVRHIAYDLRRAADDVNAQVER; (SEQ ID NO: 12)

GVRHIAYELRRAADDVNAQVER; (SEQ ID NO: 13)

GVR2IAYGLRRAADDVNAQVER; (SEQ ID NO: 14)
and

GVRE3AYGLRRAADDVNAQVER; (SEQ ID NO: 15)

wherein 2 is 2,3-Diaminopropanoic acid, and 3 is 2,4-diaminobutyric acid.

11. A method for detecting a Bfl-1-dependent cancer cell, comprising:
permeabilizing the cancer cell;
contacting the cancer cell with any one of the compounds of claim 1;
measuring the mitochondrial depolarization of the cancer cell; and
detecting a Bfl-1-dependent cancer cell when the mitochondrial depolarization is increased as compared to a control cancer cell that has not been contacted by the compound.

12. A method of detecting Bfl-1-induced resistance to chemotherapeutics in a cancer cell, comprising:
permeabilizing the cancer cell;
contacting the cancer cell with any one of the compounds of claim 1;
measuring the mitochondrial depolarization of the cancer cell; and
detecting Bfl-1-induced resistance to chemotherapeutics when the mitochondrial depolarization is increased as compared to a control cancer cell that has not been contacted by the compound.

13. A method for detecting overexpression of Bfl-1 in a cancer cell, comprising:

permeabilizing the cancer cell;
contacting the cancer cell with any one of the compounds of claim 1; and
measuring the mitochondrial depolarization of the cancer cell; and
detecting overexpression of Bfl-1 when the mitochondrial depolarization is increased as compared to a control cancer cell that has not been contacted by the compound.

14. A method for detecting a Bfl-1-dependent cancer cell, comprising:
permeabilizing the cancer cell;
contacting the cancer cell with any one of the compounds of claim 10,
measuring the mitochondrial depolarization of the cancer cell; and
detecting a Bfl-1-dependent cancer cell when the mitochondrial depolarization is increased as compared to a control cancer cell that has not been contacted by the compound.

15. A method of detecting Bfl-1-induced resistance to chemotherapeutics in a cancer cell, comprising:
permeabilizing the cancer cell;
contacting the cancer cell with any one of the compounds of claim 10;
measuring the mitochondrial depolarization of the cancer cell; and
detecting Bfl-1-induced resistance to chemotherapeutics when the mitochondrial depolarization is increased as compared to a control cancer cell that has not been contacted by the compound.

16. A method for detecting overexpression of Bfl-1 in a cancer cell, comprising:
permeabilizing the cancer cell;
contacting the cancer cell with any one of the compounds of claim 10,
measuring the mitochondrial depolarization of the cancer cell; and
detecting overexpression of Bfl-1 when the mitochondrial depolarization is increased as compared to a control cancer cell that has not been contacted by the compound.

* * * * *